(12) United States Patent
Berdis et al.

(10) Patent No.: US 9,988,680 B2
(45) Date of Patent: Jun. 5, 2018

(54) NON-NATURAL NUCLEOSIDES AS THERANOSTIC AGENTS

(75) Inventors: Anthony J. Berdis, Cleveland Heights, OH (US); Irene Lee, Cleveland Heights, OH (US); Edward Motea, Dallas, TX (US)

(73) Assignee: Case Western Reserve University, Cleveland, OH (US)

( * ) Notice: Subject to any disclaimer, the term of this patent is extended or adjusted under 35 U.S.C. 154(b) by 376 days.

(21) Appl. No.: 14/342,502

(22) PCT Filed: Sep. 4, 2012

(86) PCT No.: PCT/US2012/053669
§ 371 (c)(1),
(2), (4) Date: Jun. 10, 2014

(87) PCT Pub. No.: WO2013/033705
PCT Pub. Date: Mar. 7, 2013

(65) Prior Publication Data
US 2014/0329236 A1 Nov. 6, 2014

Related U.S. Application Data

(60) Provisional application No. 61/530,179, filed on Sep. 1, 2011.

(51) Int. Cl.
*C12Q 1/68* (2018.01)
*C07H 19/04* (2006.01)
*C07H 19/20* (2006.01)
*C07H 19/044* (2006.01)
*G01N 33/574* (2006.01)

(52) U.S. Cl.
CPC ......... *C12Q 1/6876* (2013.01); *C07H 19/044* (2013.01); *G01N 33/57407* (2013.01); *G01N 2800/52* (2013.01); *G01N 2800/56* (2013.01)

(58) Field of Classification Search
CPC ............... C07H 19/044; C12C 1/6876; G01N 33/57407; G01N 2800/52; G01N 2800/56
See application file for complete search history.

(56) References Cited

U.S. PATENT DOCUMENTS

| | | | |
|---|---|---|---|
| 5,401,724 A | 3/1995 | Beutler | |
| 5,446,139 A | 8/1995 | Seela et al. | |
| 5,478,852 A | 12/1995 | Olefsky et al. | |
| 6,153,594 A | 11/2000 | Hydro | |
| 6,548,486 B1 | 4/2003 | Dalen | |
| 7,759,470 B2 * | 7/2010 | Heindl | C07H 19/04 435/6.12 |
| 8,114,847 B2 * | 2/2012 | Berdis | C07H 19/00 514/42 |
| 8,981,078 B2 * | 3/2015 | Berdis | C07H 19/00 435/325 |
| 9,029,345 B2 * | 5/2015 | Berdis | A61K 31/70 514/42 |
| 2005/0272676 A1 | 12/2005 | Bhat et al. | |
| 2006/0025375 A1 | 2/2006 | Gosselin et al. | |
| 2007/0196852 A1 | 8/2007 | Heindl | |
| 2007/0259832 A1 | 11/2007 | Cook et al. | |
| 2009/0048202 A1 | 2/2009 | Berdis et al. | |

FOREIGN PATENT DOCUMENTS

| | | |
|---|---|---|
| WO | 1998039967 | 9/1998 |
| WO | 02/29003 A2 | 4/2002 |
| WO | 2006/101911 A1 | 9/2006 |
| WO | 2008/052775 A2 | 5/2008 |

OTHER PUBLICATIONS

Costigan, Christine, et al., "A Synthetic Lethal Screen Identifies SLK1, a Novel Protein Kinase Homolog Implicated in Yeast Cell Morphogenesis and Cell Growth", Molecular and Cellular Biology, Mar. 1992, p. 1162-1178.
Devadoss, Babho, et al., "Is a Thymine Dimer Replicated via a Transient Abasic Site Intermediate? A Comparitivs Study Using Non-Natural Nucloetides", Biochemistry 2007, 46, 4486-4498.
Grieb, Pawel, et al., "5'Esters of 2'deoxyadenosine and 2-chloro-2'-deoxyadenosine with cell differentiation-provoking agents", Acta Biochimica Polonica, vol. 49, No. Jan. 2002, p. 129-137.
Zhang, Xuemei, et al., "Rational Attempts to Optimize Non-Natural Nucleotides for Selective Incorporation Opposite an Abasic Site", Biochemistry 2006, 45, 13293-13303.
Zhang, Xuemei, et al., "Hydrophobocity, Shape, and ∏-Electron Contributions during Translesion DNA Synthesis", J. Am. Chem. Soc. 2006. 128, 143-149.
Zhang, Xuemei, et al., "A Potential Chemotherapeutic Strategy for the Selective Inhibition of Promutagenic DNA Synthesis by Non-natural Nucleotides", Biochemistry 2005, 44, 13111-13121.
Reineks, E.Z., et al., "Evaluating the contribution of base stacking during translesion DNA replication", Biochemistry, 2004, vol. 43, No. 2, pp. 393-404.
Girgis, N.S., et al., "Synthesis of 2'deoxyribofuranosyl indole nucleosides related to the antibiotics SF-2140 neosidomycin", Journal of Heterocyclic Chemistry, 2009, vol. 25, No. 2, pp. 361-366.
Motea, E.A., et al., "A non-natural nucleoside with combined therapeutic and diagnostic activities against leukemia", ACS Chemical Biology, Mar. 5, 2012, vol. 7, No. 6, pp. 988-998.
Seela et al. "Oligonucleotides containing 7-Deaza-2'-deoxyinosine as Universal Nucleoside: Synthesis of 7-Haloegenated and 7-Alkynylated Derivatives, Ambiguous Base Pairing, and Dye Functionalization by the Alkyne-Azide 'Click' Reaction", Helvetica Chimica Acta, vol. 91 (2008).

(Continued)

Primary Examiner — Lawrence E Crane
(74) Attorney, Agent, or Firm — Tarolli, Sundheim, Covell & Tummino LLP

(57) ABSTRACT

A composition for monitoring DNA damage includes a 3-ethynyl-5-nitroindolyl-2'-deoxyribose compound or pharmaceutically acceptable salt thereof and a detectable moiety with a click-reactive functional group that is complementary to the alkyne group of the compound.

6 Claims, 8 Drawing Sheets

(56) References Cited

OTHER PUBLICATIONS

Ming, et al. "Azide-alkyne "click" reaction performed on oligonucleotides with the universal nucleoside 7-octadiynyl-7-deaza-2'-deoxyinosine", Nucleic Acids Symposium Series No. 52, 471-472, Sep. 8, 2008.
Motea, et al. "Development of a 'clickable' non-natural nucleotide to visualize the replication of non-instructional DNA lesions", Nucleic Acids Research, 2012, vol. 40, No. 5, 2357-2367.
European Office Action dated Jul. 3, 2015.

* cited by examiner

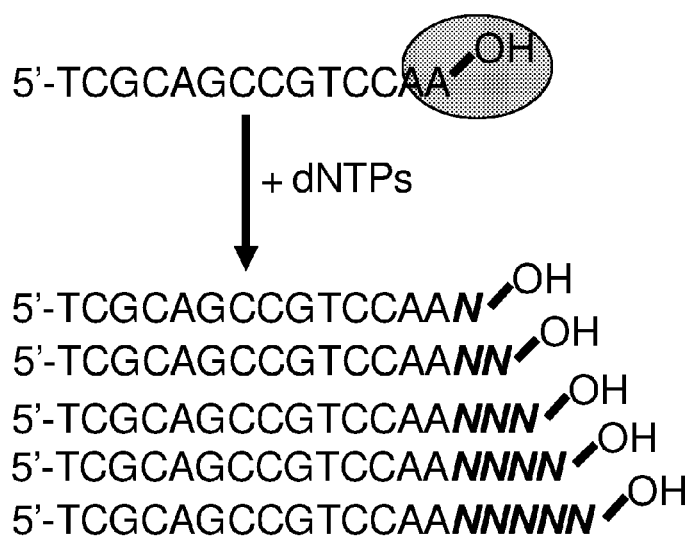
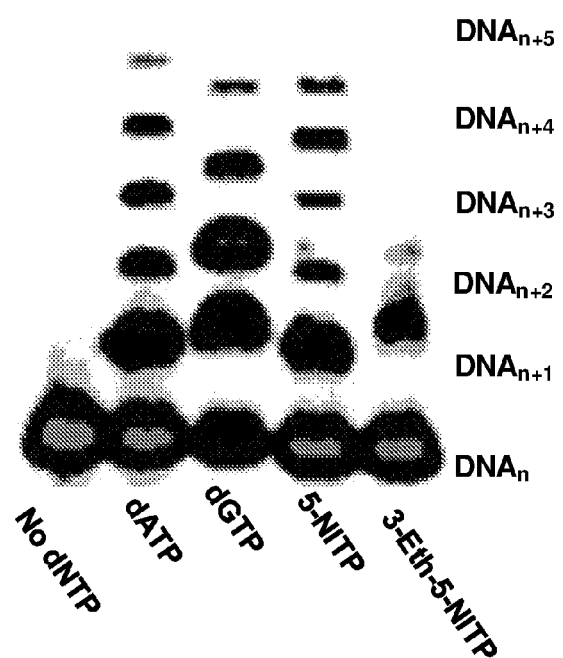
Figs. 2A-B

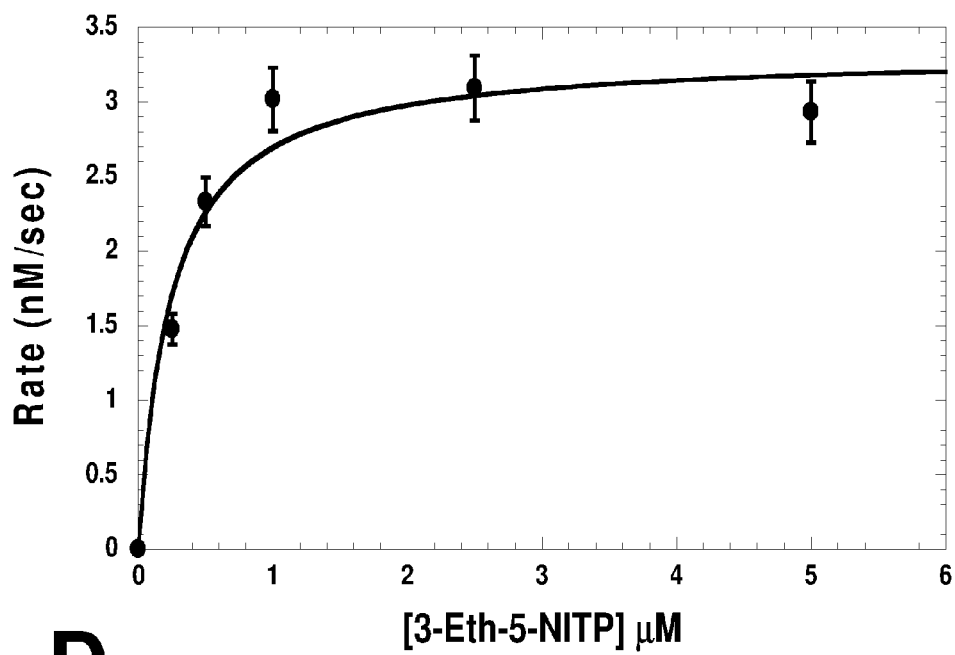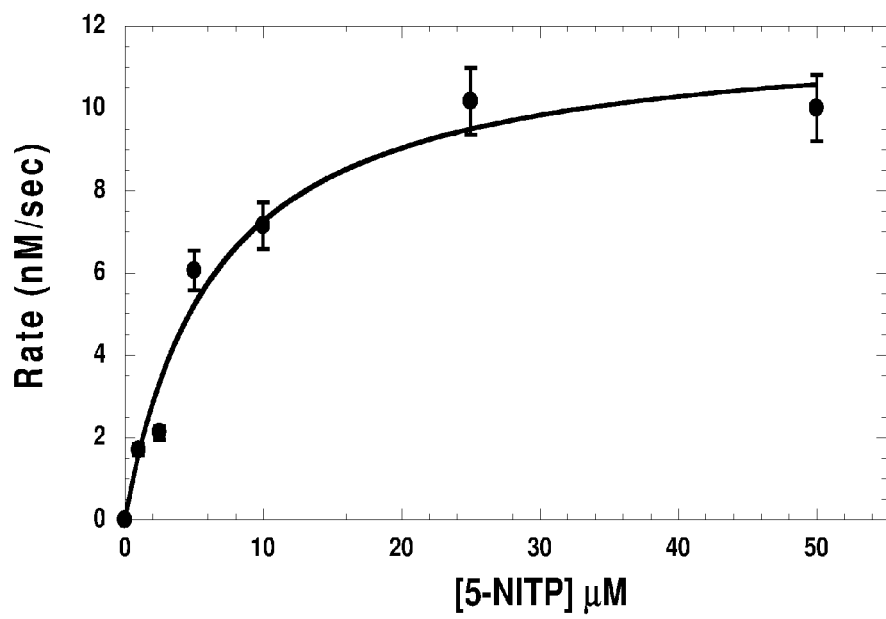
Figs. 2C-D

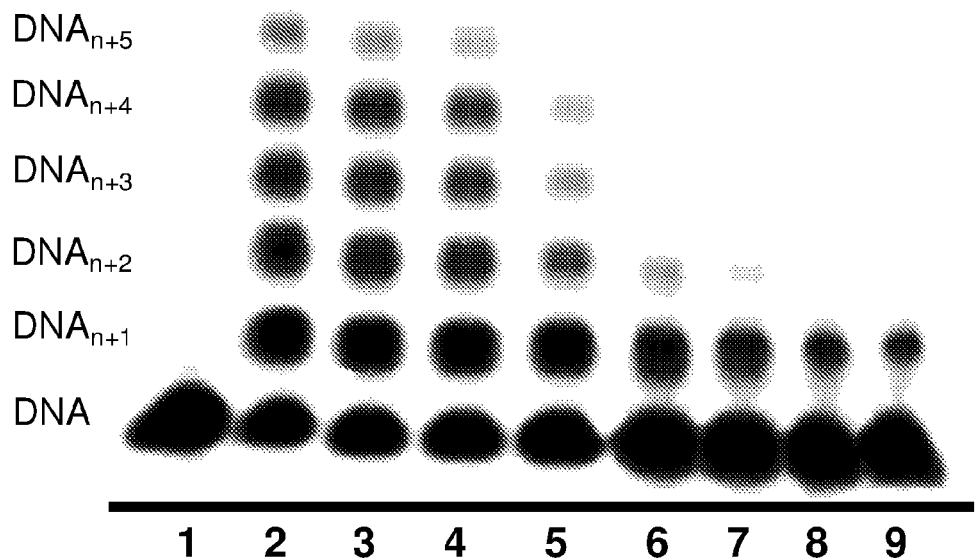
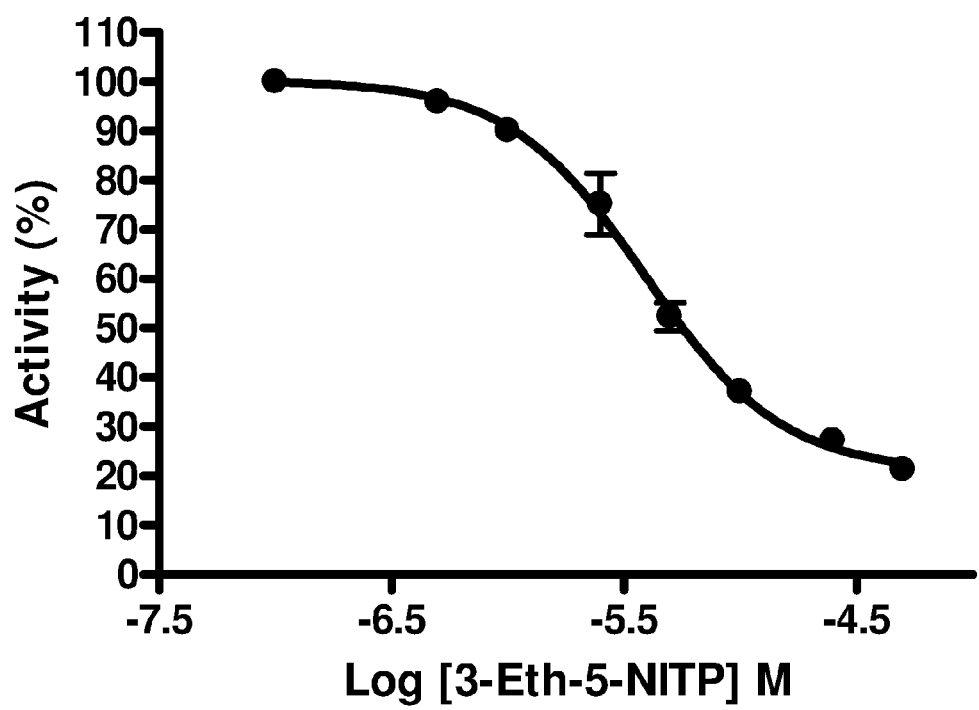
Figs. 2E-F

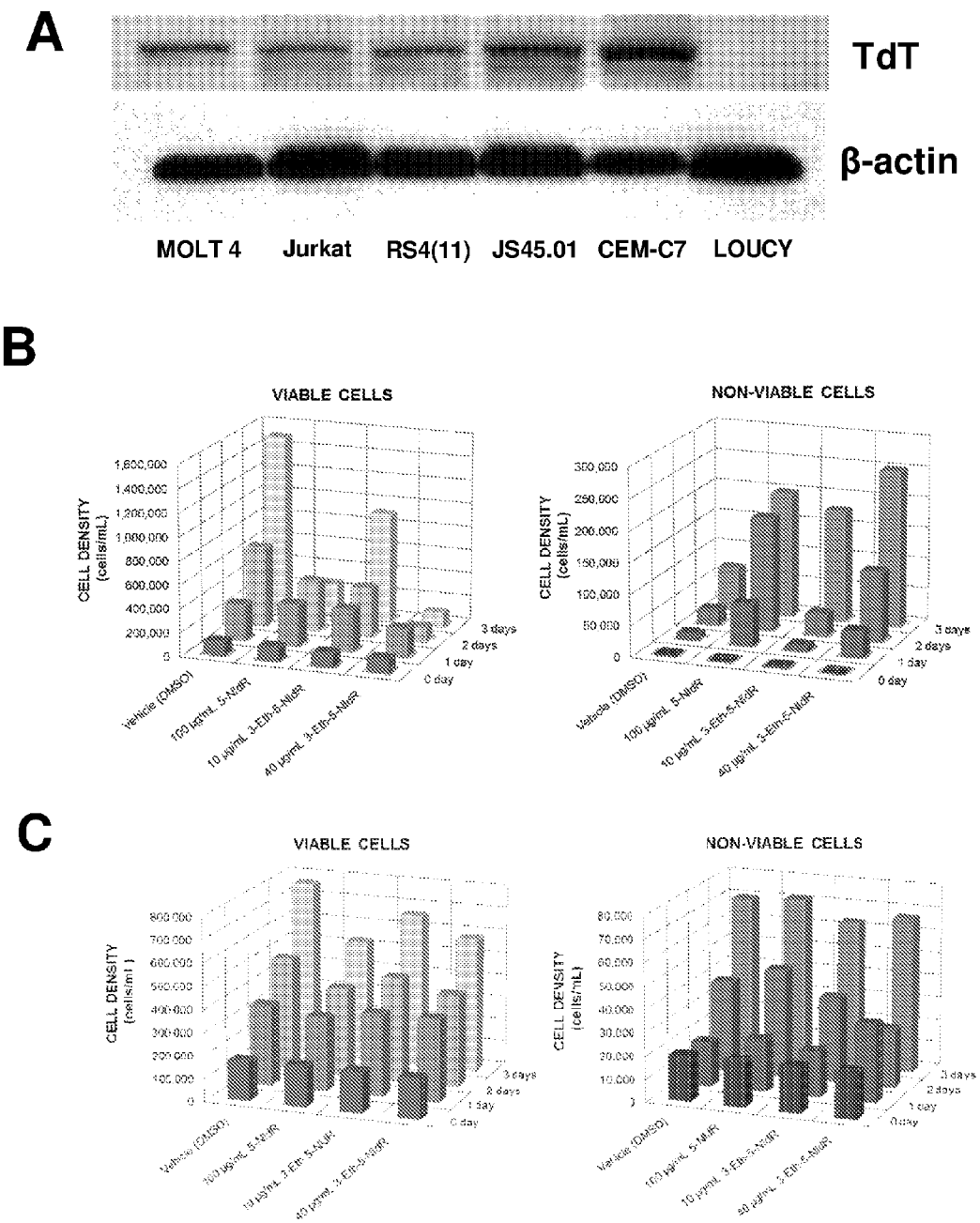
Figs. 3A-C

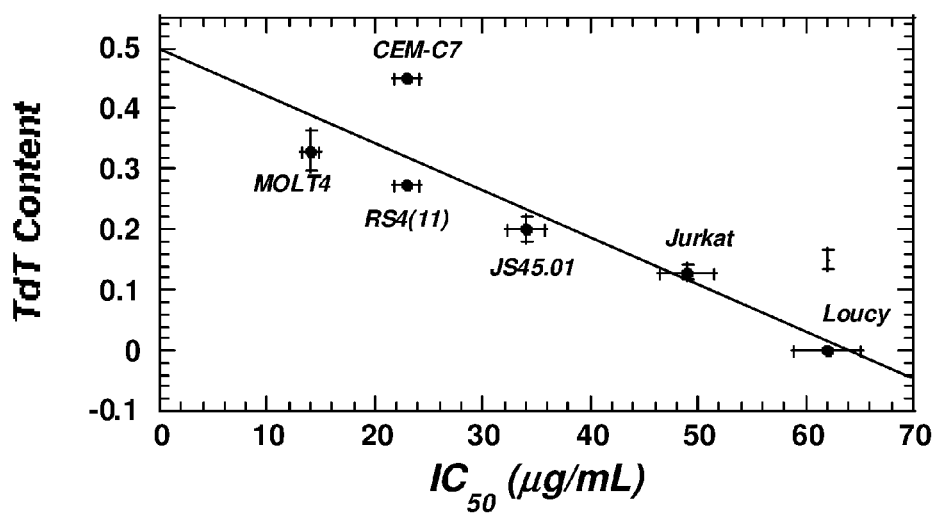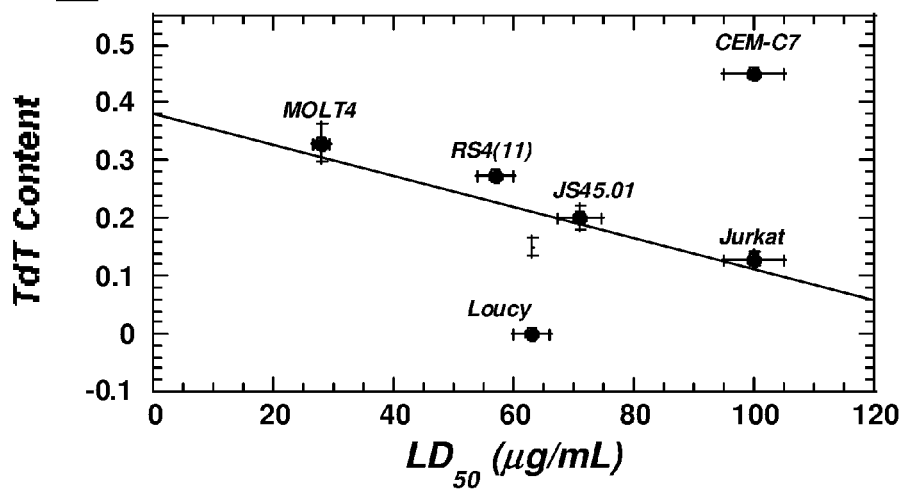
Figs. 3D-E

1. Modifications to nucleobase allow selective targeting of DNA polymerases involved in cancer
2. Natural deoxyribose moiety allows for more favorable pharmacokinetic properties (transport, metabolism, etc.)
3. Inclusion of alkyne moiety allows for covalently attachment of fluorogenic probes

NON-NATURAL NUCLEOSIDES AS THERANOSTIC AGENTS

RELATED APPLICATION

This application claims priority from U.S. Provisional Application No. 61/530,179, filed Sep. 1, 2011, the subject matter of which is incorporated herein by reference in its entirety.

GOVERNMENT FUNDING

This invention was made with government support under Grant No. CA11408 awarded by The National Cancer Institute. The United States government has certain rights to the invention.

TECHNICAL FIELD

This application relates to selective inhibitors of translesion DNA replication and to methods of using such inhibitors for therapeutic and diagnostic applications.

BACKGROUND

Chemotherapeutic agents that compromise the integrity of nucleic acid are important components in modern medical efforts to combat hyperproliferative diseases, such as cancer and autoimmune dysfunctions as well as viral and microbial infections. Many compounds, such as BCNU, cyclophosphamide, and cisplatin are effective chemotherapeutic agents because they significantly modify nucleic acid and inhibit DNA synthesis and/or DNA repair to prevent cellular proliferation. However, the widespread use of these agents is limited by two major complications. First, they are non-selective DNA damaging agents. Second, these agents induce lesions that if inappropriately replicated can cause further mutagenic events to potentiate oncogenesis. Translesion DNA synthesis also represents a possible route for the initiation of drug resistance, genetic variations associated with solid tumors, and the development of secondary cancers.

These concerns have prompted the design of more selective drugs that target specific enzymes involved in nucleic acid metabolism. Arguably, the more successful of these agents are nucleotide analogs, such as AZT and acyclovir that terminate DNA polymerization. The use of these agents is historically associated with the treatment of viruses, such as HIV and herpes simplex virus. However, they and other analogs, such as araC and fludarabine have also been used in the treatment of cancer. Unfortunately, the therapeutic utility of these nucleotide analogs is often limited by complications. The most prevalent of these complications is the excision of the enzymatically-inserted nucleotide from the primer-template to reverse chain termination, which allows for the re-initiation of DNA synthesis. Although viral polymerases use pyrophosphorolysis to remove chain terminators from DNA, eukaryotes use exonuclease proofreading activity to effectively excise the inserted chain terminator. Either activity provides a mechanism for drug resistance. Another complication is that these inhibitors contain alterations in the ribose moiety while the nucleobase portion remains identical to that of a natural nucleoside. As a consequence, there is an intrinsic lack of selectivity for inhibiting one DNA polymerase versus another. Since these agents resemble their natural counterparts, they may be degraded by cellular enzymes that metabolize natural nucleotides. For example, this complication limits the use of fludarabine and may play a significant role in the development of drug resistance to other natural nucleoside analogs.

Acute lymphocytic leukemia (ALL) is the most common form of childhood cancer. As with all cancers, a fundamental feature of ALL is its hyperproliferative nature that is defined by uncontrollable and pro-mutagenic DNA replication. Nucleoside analogues are effective anti-cancer agents against leukemia as they produce anti-proliferative and/or cytotoxic effects by inhibiting DNA replication. Despite their widespread utility, however, most nucleoside analogues possess very narrow therapeutic windows that can create significant clinical problems. This problem is exacerbated since it is nearly impossible to rapidly and accurately assess the efficacy of conventional nucleoside analogues. Patient responses to chemotherapy are typically gauged by qualitative criteria ranging from the absence of overt disease symptoms to quantifying the ratio of normal versus cancerous blood cells. These clinical end points can take weeks or even months to accurately define. As such, the inability to assess drug action on shorter time scales (hours or days) significantly hinders physicians from making informed decisions regarding optimal dosing regimens. For example analogue cordycepin (3'-deoxyadenosine) terminates DNA synthesis after its incorporation into DNA. This analogue produces cytotoxic effects against TdT-positive leukemia, especially when combined with the adenosine deaminase inhibitor, deoxycoformycin. Unfortunately, cordycepin also utilized by template-dependent DNA polymerases involved in chromosomal DNA synthesis. The ability of these polymerases to incorporate but not elongate cordycepin terminates DNA synthesis in both cancerous and healthy cells. This non-selective killing can cause adverse side effects such as immunosuppression, fatigue, nausea, vomiting, and alopecia.

SUMMARY

An embodiment of the application relates to a compound comprising formula (I):

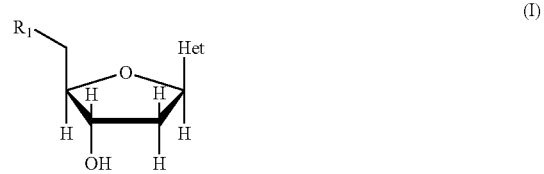

where Het is a heterocyclic azaindene analog selected from the group consisting of:

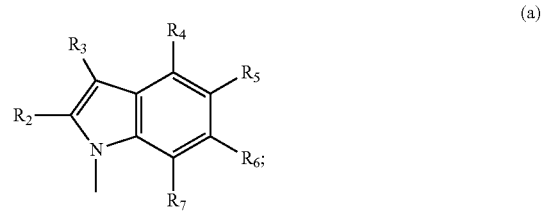

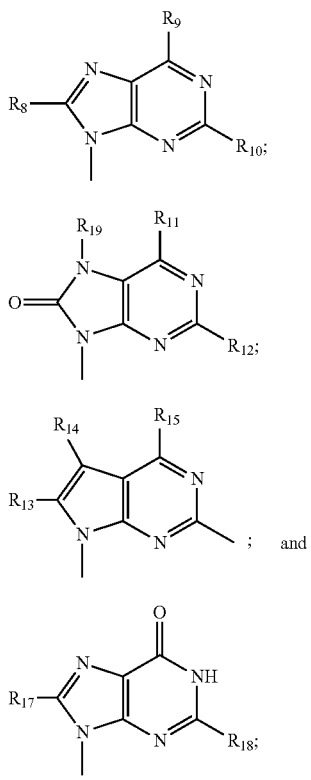

where $R_1$ is OH, monophosphate ($H_2O_3PO$— or $(O_3PO$—$)^{2-}$), diphosphate ($H_3(O_3PO)_2$— or $((O_3PO)_2$—$)^{3-}$), triphosphate ($H_4(O_3PO)_3$—, $((O_3PO)_3$—$)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate thereof;

where $R_4$, $R_5$, $R_6$, $R_7$, $R_9$, $R_{10}$, $R_{11}$, $R_{12}$, $R_{15}$, $R_{16}$, and $R_{18}$, each independently represent substituents selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(-CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O—), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O—)$_2$), phosphinato (—P(O)(O—)), phospho (—PO$_2$), phosphino (—PH$_2$), and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms; and with the proviso that at least one of $R_4$, $R_5$, $R_6$, $R_7$, $R_9$, $R_{10}$, $R_{11}$, $R_{12}$, $R_{15}$, $R_{16}$, or $R_{18}$ is other than hydrogen and that where $R_9$ is amino $R_{10}$ is other than hydrogen; and where at least one of $R_2$, $R_3$, $R_8$, $R_{13}$, $R_{14}$, $R_{17}$, or $R_{19}$ is hydrogen or a click-reactive functional group that is directly or indirectly bound to the purine or indole ring of the compound, with the proviso that at least one of $R_2$, $R_3$, $R_8$, $R_{13}$, $R_{14}$, $R_{17}$, or $R_{19}$ is other than hydrogen.

In some embodiments, the compound can be used in a method of inhibiting translesion DNA replication in a cell containing abasic nucleotides in the DNA. In other embodiments, the compound can be used in a method of treating cancer in a subject. The compound can be administered alone or with a therapeutic agent. The therapeutic agent can include at least one of a chemotherapeutic agent, an antimetabolite, an antitumorgenic agent, an antimitotic agent, an antiviral agent, an antineoplastic agent, an immunotherapeutic agent, and a radiotherapeutic agent. The therapeutic agent can also include at least one cytoxic agent or DNA damaging agent that can compromise the integrity of nucleic acids associated with DNA replication and cellular proliferation.

Other embodiments described herein relate to a method of monitoring DNA damage in cancer cells of a subject using the compound. The method can include administering the compound to cancer cells of the subject and administering to the cancer cells a detectable moiety with a click-reactive functional group that is complementary to the click-reactive functional group of the compound. The detectable moiety can bind to the compound and then be detected to determine DNA damage and chain termination in the cancer cells. In some aspects, the DNA damage can be caused by a DNA damaging agent that generates abasic sites in the DNA and the method can be used to monitor the efficacy of the DNA damaging agent and the compound in treating the cancer.

BRIEF DESCRIPTION OF THE DRAWINGS

FIGS. 2(A-F) illustrate non-natural nucleotides are efficient substrates for terminal deoxynucleotidyl transferase. (A) DNA substrate (SEQ ID NOs.: 1-6) and assay used to monitor nucleotide incorporation catalyzed by TdT. (B) Denaturing gel electrophoresis image for the incorporation and extension of dATP, dGTP, 5-NITP, and 3-Eth-5-NITP by TdT. Data points were obtained by quenching an aliquot of the reaction in EDTA (Δt=2 min). (C) Michaelis-Menten plot for the incorporation of 3-Eth-5-NITP by TdT. Rates of incorporation (closed circle) were plotted against 3-Eth-5-

NITP concentration. A fit of the data to the Michaelis-Menten equation yielded a Vmax of 3.2±0.1 nM s-1 and a Km of 0.19±0.04 μM. (D) Michaelis-Menten plot for the incorporation of 5-NITP by TdT. Rates of incorporation (closed circle) were plotted against 5-NITP concentration. A fit of the data to the Michaelis-Menten equation yielded a Vmax of 11.5±0.4 nM s-1 and a Km of 4.6±0.6 μM. (E) Representative gel image illustrating the dose dependence of the chain-termination capabilities of 3-Eth-5-NITP. The assay was performed using 6 units of TdT preincubated with 1.5 μM 32Pradio-labeled 14-mer DNA substrate in 100 mM cacodylate buffer (pH 6.8) containing 1 mM $CoCl_2$ and 0.1 mM DTT. The reaction was initiated by the addition of 10 μM dNTPs in the absence and presence of 3-Eth-5-NITP. Lane 1=14-mer DNA alone. Lane 2=10 μM dNTPs. Lane 3=10 μM dNTPs+0.5 μM 3-Eth-5-NITP. Lane 4=10 μM dNTPs+1 μM 3-Eth-5-NITP. Lane 5=10 μM dNTPs+2.5 μM 3-Eth-5-NITP. Lane 6=10 μM dNTPs+5 μM 3-Eth-5-NITP. Lane 7=10 μM dNTPs+10 μM 3-Eth-5-NITP. Lane 8=10 μM dNTPs+25 μM 3-Eth-5-NITP. Lane 9=10 μM dNTPs+50 μM 3-Eth-5-NITP. Data points were obtained by quenching an aliquot of the reaction in EDTA (Δt=2 min). (F) Dose-response curve used to calculate an IC50 value of 3.9±1.0 μM. The IC50 value of 3.9±1.0 μM represents an average from three independent experiments performed as described in the text.

FIGS. 3(A-E) illustrate the anti-cancer effects of non-natural nucleosides with cellular levels of TdT. (A) Western blot analyses examining TdT content in ALL cell lines including MOLT4, Jurkat, RS4(11), JS45.01, CEM-C7, and Loucy. TdT content was normalized against cellular levels of β-actin in each respective cell line. (B) Time courses in the number of viable (left) and non-viable (right) MOLT4 cells in the absence and presence of non-natural nucleosides. (C) Time courses in the number of viable (left) and non-viable (right) Loucy cells in the absence and presence of nonnatural nucleosides. (D) Plot correlating IC50 values of 3-Eth-5-NIdR against various ALL cell lines versus the cellular content of TdT in each cell line. (E) Plot correlating LD50 values of 3-Eth-5-NIdR against various ALL cell lines versus the respective cellular content of TdT in each ALL cell line.

Figure 4A:
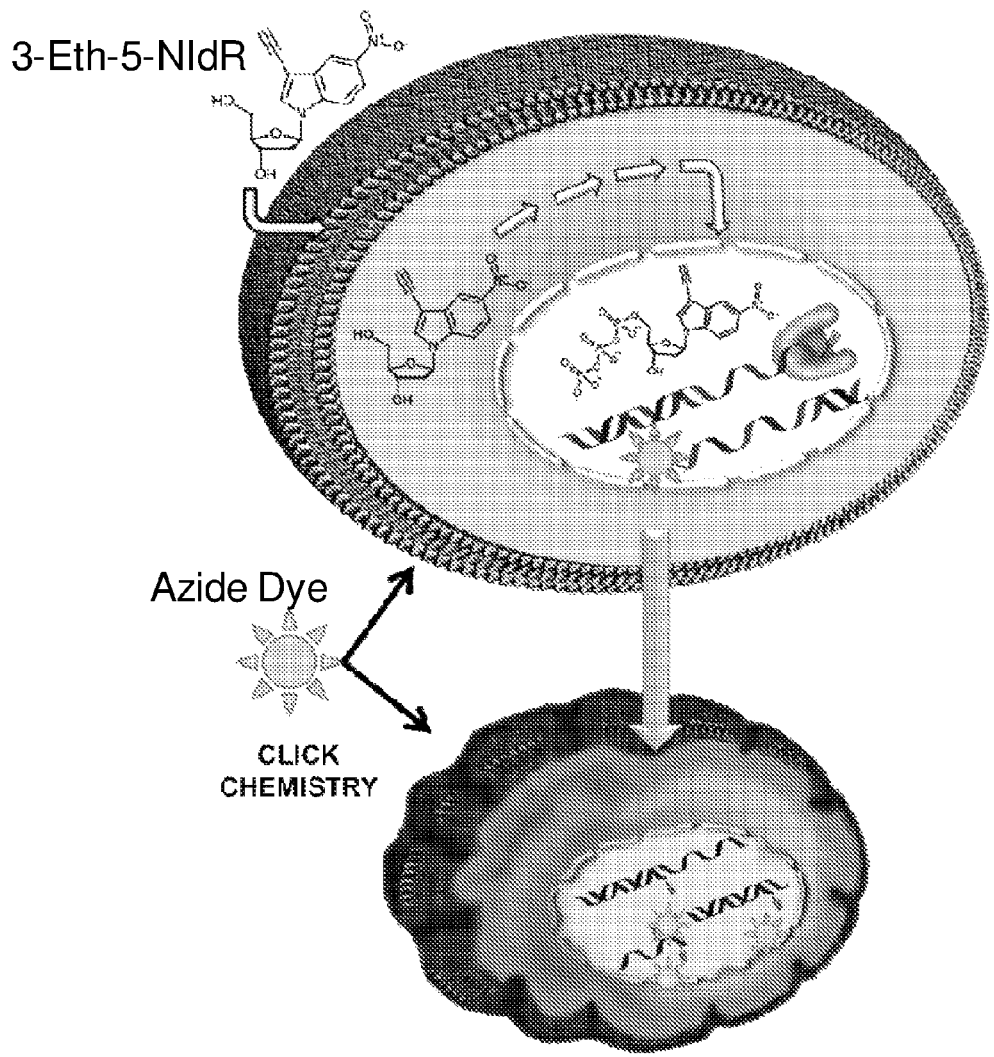
Figure 4B:
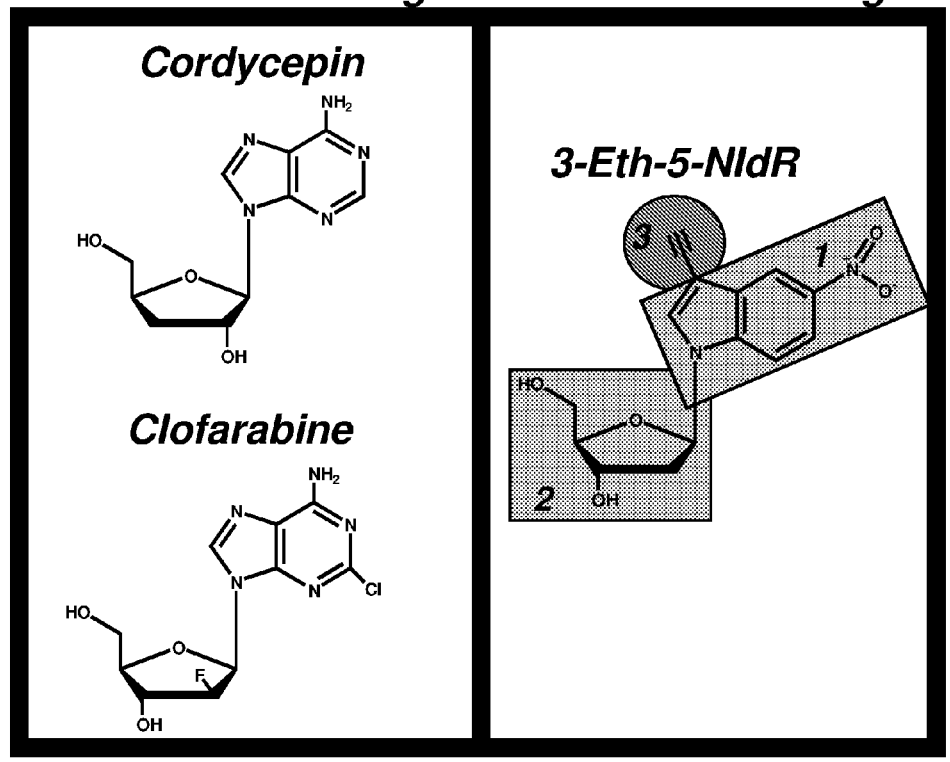

FIGS. 4(A-B) illustrate a schematic drawing of diagnostic applications of non-natural nucleotides. (A-B) Structural comparison between conventional nucleoside analogues (cordycepin and clofarabine) with the non-natural nucleoside 3-Eth-5-NIdR.

DETAILED DESCRIPTION

The terms used in this specification generally have their ordinary meanings in the art, within the context of this disclosure and in the specific context where each term is used. Certain terms are discussed below, or elsewhere in the specification, to provide additional guidance to the practitioner in describing the compositions and methods and how to make and use them.

The articles "a" and "an" are used herein to refer to one or to more than one (i.e., to at least one) of the grammatical object of the article. By way of example, "an element" means one element or more than one element.

The phrase "having the formula" or "having the structure" is not intended to be limiting and is used in the same way that the term "comprising" is commonly used.

The term "alkyl" refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups, such as cyclopentyl, cyclohexyl, and the like. Generally, although again not necessarily, alkyl groups herein contain 1 to about 18 carbon atoms, preferably 1 to about 12 carbon atoms. The term "lower alkyl" intends an alkyl group of 1 to 6 carbon atoms. Substituents identified as "$C_1$-$C_6$ alkyl" or "lower alkyl" can contain 1 to 3 carbon atoms, and more particularly such substituents can contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituen, in which at least one carbon atom is replaced with a heteroatom, as will be described in further detail infra. If not otherwise indicated, the term "aryl" includes unsubstituted, substituted, and/or heteroatom-containing aromatic substituents.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 20 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctyl-naphthyl, 3-ethyl-cyclopenta-1,4-diene, and the like.

The term "cyclic" refers to alicyclic or aromatic substituents that may or may not be substituted and/or heteroatom containing, and that may be monocyclic, bicyclic, or polycyclic.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

"Hydrocarbyl" refers to univalent hydrocarbyl radicals containing 1 to about 30 carbon atoms, preferably 1 to about 24 carbon atoms, more preferably 1 to about 18 carbon atoms, most preferably about 1 to 12 carbon atoms, including linear, branched, cyclic, saturated, and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano(-CN), isocyano (—$N^+C^-$), cyanato (—O—CN), isocyanato (—$ON^+C^-$), isothiocyanato (—S—CN), azido (—N=$N^+$=$N^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$SO_2$—$O^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)($O^-$)$_2$), phosphinato (—P(O)(O—)), phospho (—$PO_2$), and phosphino (—$PH_2$); and the hydrocarbyl moieties $C_1$-$C_{24}$ alkyl (preferably $C_1$-$C_{18}$ alkyl, more preferably $C_1$-$C_{12}$ alkyl, most preferably $C_1$-$C_6$ alkyl), $C_2$-$C_{24}$ alkenyl (preferably $C_2$-$C_{18}$ alkenyl, more preferably $C_2$-$C_{12}$ alkenyl, most preferably $C_2$-$C_6$ alkenyl), $C_2$-$C_{24}$ alkynyl (preferably $C_2$-$C_{18}$ alkynyl, more preferably $C_2$-$C_{12}$ alkynyl, most preferably $C_2$-$C_6$ alkynyl), $C_5$-$C_{20}$ aryl (preferably $C_5$-$C_{14}$ aryl), $C_6$-$C_{24}$ alkaryl (preferably $C_6$-$C_{18}$ alkaryl), and $C_6$-$C_{24}$ aralkyl (preferably $C_6$-$C_{18}$ aralkyl).

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl."

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

When referring to a "compound" or "agent" herein, the term "compound" or "agent" is meant to encompass not only the specified molecular entity but also its pharmaceutically acceptable, pharmacologically active analogs, including, but not limited to, salts, esters, amides, prodrugs, conjugates, active metabolites, and other such derivatives, analogs, and related compounds.

As used herein, the terms "cancer cell" or "tumor cell" can refer to cells that divide at an abnormal (i.e., increased) rate. Cancer cells include, but are not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, meningoma, medulloblastoma, schwannoma and epidymoma.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" derivative or analog, refers to a derivative or analog having the same type of pharmacological activity as the parent compound and approximately equivalent in degree.

As used herein, the term "pharmaceutically acceptable salts" or complexes refers to salts or complexes of the nucleosides that retain the desired biological activity of the parent compound and exhibit minimal, if any, undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, palmoic acid, alginic acid, polyglutamic acid, naphthalenesulfonic acids, naphthalenedisulfonic acids, and polygalacturonic acid; (b) base addition salts formed with cations such as sodium, potassium, zinc, calcium, bismuth, barium, magnesium, aluminum, copper, cobalt, nickel, cadmium, sodium, potassium, and the like, or with an organic cation formed from N,N-dibenzylethylene-diamine, ammonium, or ethylenediamine; or (c) combinations of (a) and (b); e.g., a zinc tannate salt or the like.

The term "prodrug", as used herein, refers to a compound that is converted into the nucleoside on administration in vivo. Nonlimiting examples are pharmaceutically acceptable salts (alternatively referred to as "physiologically acceptable salts).

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The term "monitoring" as used herein refers to the use of results generated from datasets to provide useful information about an individual or an individual's health or disease status. "Monitoring" can include, for example, determination of prognosis, risk-stratification, selection of drug therapy, assessment of ongoing drug therapy, determination of effectiveness of treatment, prediction of outcomes, determination of response to therapy, diagnosis of a disease or disease complication, following of progression of a disease or providing any information relating to a patient's health status over time, selecting patients most likely to benefit from experimental therapies with known molecular mechanisms of action, selecting patients most likely to benefit from approved drugs with known molecular mechanisms where that mechanism may be important in a small subset of a disease for which the medication may not have a label, screening a patient population to help decide on a more invasive/expensive test, for example, a cascade of tests from a non-invasive blood test to a more invasive option such as biopsy, or testing to assess side effects of drugs used to treat another indication.

The term "quantitative data" or "quantitative level" or "quantitative amount" as used herein refers to data, levels, or amounts associated with any dataset components (e.g., markers, clinical indicia,) that can be assigned a numerical value.

The term "subject" as used herein refers to a human or another mammal, that can be afflicted by a cancer or a neoplastic disease, including leukemia, but may or may not have such a disease. Typically, the terms "subject" and "patient" are used herein interchangeably in reference to a mammal.

As used herein, the term "subject suspected of having cancer" refers to a subject that presents one or more symptoms indicative of cancer or that is being screened for cancer (e.g., during a routine physical examination). A subject suspected of having cancer may also have one or more risk factors. The term encompasses individuals who have not been tested for cancer, individuals who have received an initial diagnosis (e.g., a CT scan showing a mass) but for whom the stage of cancer is not known, as well as individuals for whom the stage and/or grade of cancer has been determined by a conventional method. The term also includes patients who have previously undergone therapy for cancer.

As used herein, the term "subject at risk for cancer" refers to a subject with one or more risk factors for developing cancer. Risk factors include, but are not limited to, gender, age, genetic predisposition, previous incidents with cancer, and pre-existing non-cancer diseases.

The terms "normal" and "healthy" are used herein interchangeably. They refer to an individual or group of individuals who have not shown any symptoms of cancer, and have not been diagnosed with cancer. Preferably, the normal individual (or group of individuals) is not on medication affecting cancer. In certain embodiments, normal individuals have similar sex, age, body mass index as compared with the individual from which the sample to be tested was obtained. The term "normal" is also used herein to qualify a sample isolated from a healthy individual.

The terms "control" or "control sample" as used herein refer to one or more biological samples isolated from an individual or group of individuals that are normal (i.e., healthy). The term "control", "control value" or "control sample" can also refer to the compilation of data derived from samples of one or more individuals classified as normal, and/or one or more individuals diagnosed with cancer.

The term "indicative of cancer" as used herein refers to a level or an amount, which is diagnostic of cancer such that the level is found significantly more often in subjects with the disease than in patients without the disease or another stage of cancer (as determined using routine statistical methods setting confidence levels at a minimum of 95%). Preferably, a level, which is indicative of cancer, is found in at least about 60% of patients who have the disease and is found in less than about 10% of subjects who do not have the disease. More preferably, a level, which is indicative of cancer, is found in at least about 70%, at least about 75%, at least about 80%, at least about 85%, at least about 90%, at least about 95% or more in patients who have the disease and is found in less than about 10%, less than about 8%, less than about 5%, less than about 2.5%, or less than about 1% of subjects who do not have the disease.

Embodiments described herein are directed to agents or compounds that are potent chain terminators of translesion DNA replication and that can selectively inhibit DNA polymerases. By acting as chain terminators, these agents are designed to selectively inhibit the propagation of genomic errors caused by translesion DNA synthesis beyond a mispair. The agents can comprise selective non-natural nucleosides (or non-natural nucleoside analogs) that have enhanced binding affinity and faster polymerization to abasic sites on mutagenic DNA than natural nucleosides and that can also act as a substrate for DNA polymerases. The in vitro studies described herein show that the non-natural nucleoside analogs are potent chain terminators for template-independent synthesis catalyzed by DNA polymerases and are poorly incorporated opposite normal templating bases. The non-natural nucleoside analogs can target and inhibit pro-mutagenic DNA synthesis, a leading culprit in disease development as well as in the development of drug resistance.

Figure 1:
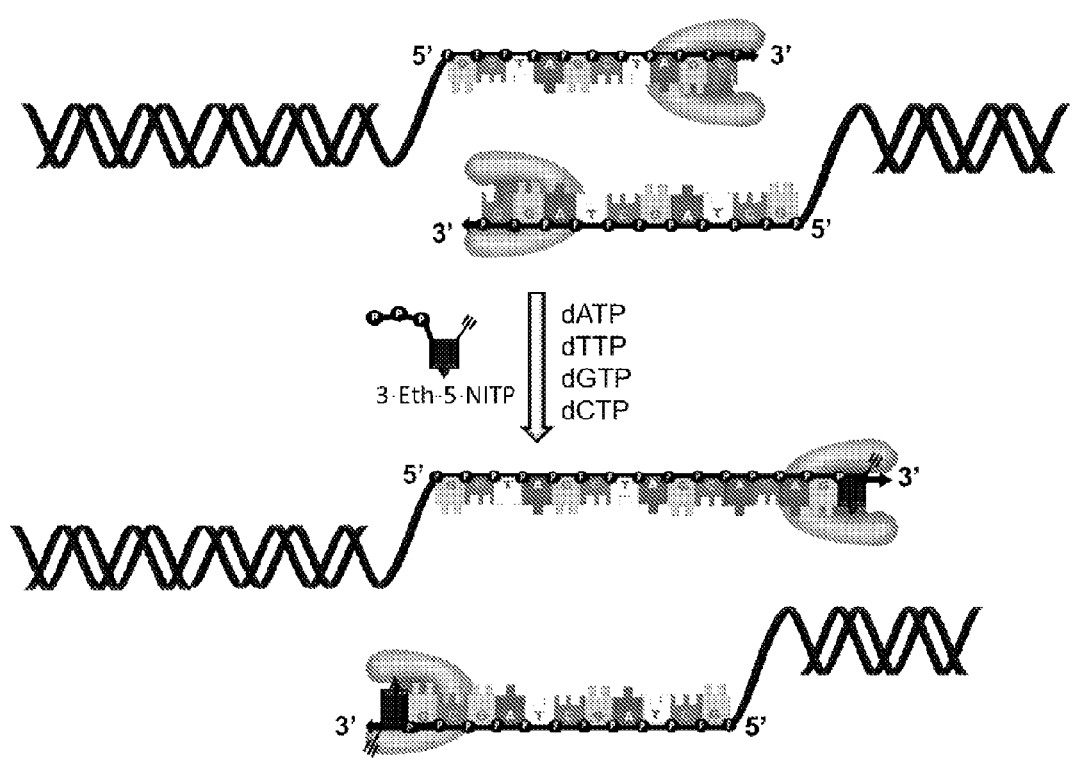
FIG. 1 illustrates a schematic drawing of a strategy for using "clickable" nucleotides to monitor template-independent DNA synthesis.

As illustrated schematically in FIG. 1, the non-natural nucleoside analogs include a click-reactive functional group that allows a detectable moiety to be attached to the analog upon or after incorporation of the non-natural nucleoside analog into DNA of a cancer cell. Attachment of the detectable moiety to the non-natural nucleoside analog allows the analog to be detected and to measure, quantify, and/or monitor the extent of the analog incorporation into DNA and cellular activity of DNA polymerases. The ability to monitor the self-effectiveness of the non-natural nucleoside analogs as an anti-cancer agent defines its function as a theranostic agent against cancer.

The non-natural nucleosides described herein can be distinguished from conventional nucleosides in at least three aspects. First, the non-natural nucleosides described herein contain a unique nucleobase devoid of classical hydrogen-bonding functional groups. Second, the presence of a click-reactive functional group allows for facile covalent attachment of detectable moieties, such as fluorogenic molecules. Finally, the non-natural nucleosides described herein contain a natural deoxyribose moiety rather than a modified sugar. All three features significantly impact the biological function of the non-natural nucleosides and allow the non-natural nucleosides to selectivity inhibit template-independent DNA synthesis. Indeed, the increased utilization of these analogues by DNA polymerases provides a reasonable mechanism to explain their higher potencies against cancer cells with such elevated DNA polymerase levels compared to those with lower levels of the DNA polymerases.

Additionally, while conventional nucleoside analogues function as effective therapeutic agents against cancers, such as leukemia, none possess diagnostic capabilities to monitor their self-effectiveness. The non-natural nucleosides described herein with click-reactive functional groups represent an important clinical feature that can be used to directly quantify the location and concentration of the non-natural nucleoside in patient samples. Theranostic agents comprising the non-natural nucleosides described herein, such as 3-Eth-5-NIdR, can allow physicians to adjust the dose of nucleoside rapidly and accurately to optimize its therapeutic effectiveness. These features can alleviate possible adverse side effects associated with chemotherapy capability and thus improve patient care by achieving optimal levels of a drug to kill cancer cells without harming normal cells.

Inclusion of a natural deoxyribose moiety in the non-natural nucleosides described herein may also provide improved pharmacokinetic features compared to conventional nucleoside analogues. For example, natural nucleosides and their anti-cancer counterparts enter cells via the activity of various equilibrative and concentrative nucleoside transporters. The major recognition element for efficient transport is the presence of a natural (deoxy)sugar moiety. Transport activity is highly sensitive to the correct sugar conformation as nucleoside analogues, such as AZT (zidovudine) and ddC (zalcitabine) that lack a 3'-hydroxyl group show poor cellular uptake. As such, the presence of an unmodified deoxyribose group on non-natural nucleosides described herein may facilitate their cellular transport and provide an advantage over conventional nucleoside analogues, such as fludarabine and gemcitabine that use modified sugar moieties to inhibit DNA synthesis. The presence of a correct deoxyribose moiety on the non-natural nucleosides described herein may also facilitate their conversion to the triphosphate form that is required for incorporation into nucleic acid.

In some embodiments, the agents or non-natural nucleoside analogs described herein can comprise an adenine deoxyribose analog that is selectively inserted opposite an abasic site of damaged or mutagenic DNA, behaves as chain terminators once inserted, and is poorly incorporated into unmodified (i.e., natural) DNA. In some aspects, the adenine deoxyriboside analog can have the following formula (I):

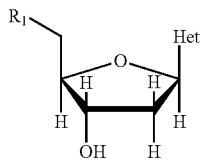

(I)

where Het is a heterocyclic azaindene analog (e.g., purine analogs or indole analogs) selected from the group consisting of:

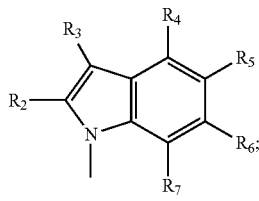

(a)

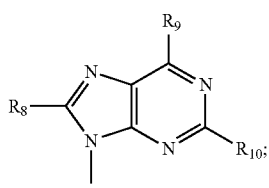

(b)

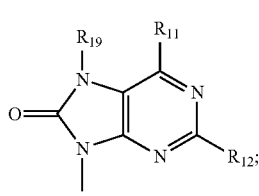

(c)

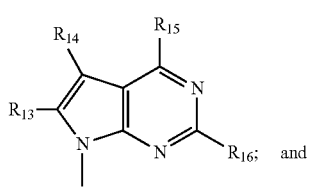

(d) and

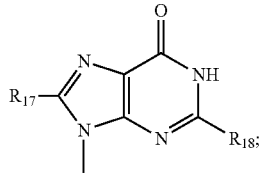

(e)

where $R_1$ is OH, monophosphate ($H_2O_3PO-$ or $(O_3PO-)^{2-}$), diphosphate ($H_3(O_3PO)_2-$ or $((O_3PO)_2-)^{3-}$), triphosphate ($H_4(O_3PO)_3-$, $((O_3PO)_3-)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate thereof;

where $R_4$, $R_5$, $R_6$, $R_7$, $R_9$, $R_{10}$, $R_{11}$, $R_{12}$, $R_{15}$, $R_{16}$, and $R_{18}$, each independently represent substituents selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O— alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano(-CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms; and with the proviso that at least one of $R_4$, $R_5$, $R_6$, $R_7$, $R_9$, $R_{10}$, $R_{11}$, $R_{12}$, $R_{15}$, $R_{16}$, $R_{18}$ is other than hydrogen and that where $R_9$ is amino $R_{10}$ is other than hydrogen; and where at least one $R_2$, $R_3$, $R_8$, $R_{13}$, $R_{14}$, $R_{17}$, or $R_{19}$ include click-reactive functional groups that are directly or indirectly bound to the purine or indole ring of the agent, a pharmaceutically acceptable salt thereof; or a prodrug thereof.

By click-reactive functional groups it is meant that the functional group has click reactivity and/or can under a click reaction with a complementary click reactive functional group. Examples of the types of reactions that are known to have click reactivity include cycloaddition reactions. These reactions represent highly specific reactant pairs that have a chemoselective nature, meaning that they mainly react with each other and not other functional groups. One example of a cycloaddition reaction is the Huisgen 1,3-dipolar cycloaddition of a dipolarophile with a 1,3 dipolar component that produce five membered (hetero)cycles. Examples of dipolarophiles are alkenes, alkynes, and molecules that possess related heteroatom functional groups, such as carbonyls and nitriles. Specifically, another example is the 2+3 cycloaddition of alkyl azides and acetylenes. Other cycloaddition reactions include Diels-Alder reactions of a conjugated diene and a dienophile (such as an alkyne or alkene).

Other examples of the types of reactions that are known to have click reactivity include a hydrosilation reaction of H—Si and simple non-activated vinyl compounds, urethane formation from alcohols and isocyanates, Menshutkin reactions of tertiary amines with alkyl iodides or alkyl trifluoromethanesulfonates, Michael additions, e.g., the very efficient maleimide-thiol reaction, atom transfer radical addition reactions between —$SO_2Cl$ and an olefin, metathesis, Staudinger reaction of phosphines with alkyl azides, oxidative coupling of thiols, many of the procedures already used in dendrimer synthesis, especially in a convergent approach, which require high selectivity and rates, nucleophilic substitution, especially of small strained rings like epoxy and aziridine compounds, carbonyl chemistry like formation of ureas, and addition reactions to carbon-carbon double bonds like dihydroxylation. Therefore, the attached click-reactive functional group may be chosen from acetylene group, an azido-group, a nitrile group, acetylenic group, amino group, phosphino group. The click chemistry reaction may results in the addition of a functional group selected from amino, primary amino, hydroxyl, sulfonate, benzotriazole, bromide, chloride, chloroformate, trimethylsilane, phosphonium bromide or bio-responsive functional group.

In some embodiments, at least one $R_2$, $R_3$, $R_8$, $R_{13}$, $R_{14}$, $R_{17}$, or $R_1$ can include, for example, an amine, sulfate, thiol, hydroxyl, azide, alkyne, alkene, carboxyl groups, aldehyde groups, sulfone groups, vinylsulfone groups, isocyanate groups, acid anhydride groups, epoxide groups, aziridine groups, episulfide groups, groups such as —$CO_2N(COCH_2)_2$, —$CO_2N(COCH_2)_2$, —$CO_2H$, —CHO, —$CHOCH_2$, —N=C=O, —$SO_2CH=CH_2$, —$N(COCH_2)_2$, —S—S—($C_5H_4N$) and groups of the following structures wherein X is halogen and R is hydrogen or $C_1$ to $C_4$ alkyl

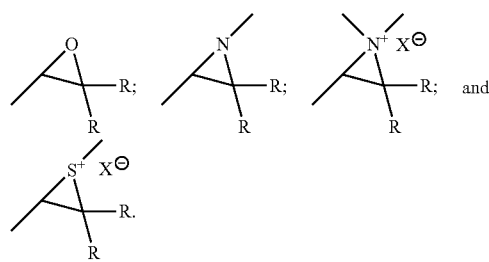

The non-natural nucleosides can be provided with click-reactive functional groups using any variety of suitable chemical processes. Those skilled in the art reading this disclosure will readily envision chemical reactions for activating treated substrate to render them suitable for use in the presently described agents.

The click-reactive functional groups can be reactive with a detectable moiety that includes a click-reactive functional group that is complementary to the click-reactive functional group of the non-natural nucleoside. By complementary, it is meant the click-reactive functional groups of detectable moiety are able to interact with the click-reactive functional group of the non-natural nucleoside to covalently bond the detectable moiety to the non-natural nucleoside.

In some embodiments, the detectable moiety can include optically detectable moieties, such as a chromophore, luminophore, fluorophore, quantum dot or nanoparticle light scattering label; electromagnetic spin label; calorimetric agent; magnetic substance; electron-rich material such as a metal; electrochemiluminescent label; moiety that can be detected based on a nuclear magnetic, paramagnetic, electrical, charge to mass, or thermal characteristic; light scattering or plasmon resonant materials, such as gold or silver particles; or multielement reporter systems, such as affinity tags including but not limited to enzyme and substrate reporter groups. Fluorophores that can potentially be used include, for example, fluorescent lanthanide complexes, including those of Europium and Terbium, fluorescein, fluorescein isothiocyanate, dichlorotriazinylamine fluorescein, rhodamine, tetramethylrhodamine, umbelliferone, eosin, erythrosin, coumarin, methyl-coumarins, pyrene, Malacite green, Cy3, Cy5, Cy5.5, stilbene, Lucifer Yellow, Cascade Blue, Texas Red, alexa dyes, dansyl chloride, phycoerythin, luciferin, green fluorescent protein and its wavelength shifted variants, bodipy, and others known in the art such as those described in Haugland, Molecular Probes Handbook, (Eugene, Oreg.) 6th Edition; The Synthegen catalog (Houston, Tex.), Lakowicz, Principles of Fluorescence Spectroscopy, 2nd Ed., Plenum Press New York (1999), or WO 98/59066.

In some aspects, the detectable moiety upon covalent bonding to the non-natural nucleoside analog described herein may be used in conjunction with non-invasive imaging techniques for in vivo or in vitro imaging of the detectable moiety and the cancer cell. Examples of imaging modalities include magnetic resonance spectroscopy (MRS) or imaging (MRI), gamma imaging, such as positron emission tomography (PET) or single-photon emission computed tomography (SPECT), near infrared (NIR) imaging, fluorescent microscopy, and mutiphoton microscopy. For purposes of in vivo or in vitro imaging, the type of detection instrument available is a major factor in selecting a given detectable moiety.

In some embodiments, the click-reactive functional group of the non-natural nucleoside can be an alkyne group and the detectable moiety can comprise a fluorescent moiety or fluorophore that includes an azide group. The fluorescent moiety can be, for example, a coumarin, rhodamine, xanthene, fluorescein, and/or cyanine dye that allow ready detection of the non-natural nucleoside upon covalent bonding to the non-natural nucleoside via the click reaction.

In one subclass of theranostic agents, the adenine deoxyribose analog can comprise an indolyl deoxyribose analog that is substituted at the 4-position, the 5-position, and/or the 6-position of the indole analog, such as shown in the following formula (II):

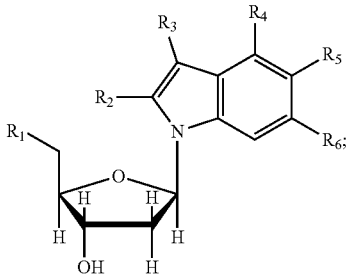

(II)

where $R_1$ is OH, monophosphate ($H_2O_3PO-$ or $(O_3PO-)^{2-}$), diphosphate ($H_3(O_3PO)_2-$ or $((O_3PO)_2-)^{3-}$), triphosphate ($H_4(O_3PO)_3-$, $((O_3PO)_3-)^{4-}$), or $OR_a$, where $R_a$ comprises at least one of a straight chain, branched or cylclic alkyl, CO-alkyl, CO-aryl, CO-alkoxyalkyl, arylsulfonyl, aralkylsulfonyl, amino acid residude, fatty acid residue, or a mono, di, or triphosphate thereof;

where $R_4$, $R_5$, and $R_6$ each independently represent substituents selected from the group consisting of hydrogen, $C_1$-$C_{24}$ alkyl, $C_2$-$C_{24}$ alkenyl, $C_2$-$C_{24}$ alkynyl, $C_3$-$C_{20}$ aryl, $C_6$-$C_{24}$ alkaryl, $C_6$-$C_{24}$ aralkyl, halo, hydroxyl, $C_1$-$C_{24}$ alkoxy, $C_2$-$C_{24}$ alkenyloxy, $C_2$-$C_{24}$ alkynyloxy, $C_5$-$C_{20}$ aryloxy, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms; and with the proviso that at least one of $R_4$, $R_5$, and $R_6$, is other than hydrogen; and where $R_2$ or $R_3$ is a click-reactive functional group selected from the group consisting of an amine, sulfate, thiol, hydroxyl, azide, alkyne, alkene, carboxyl groups, aldehyde groups, sulfone groups, vinylsulfone groups, isocyanate groups, acid anhydride groups, epoxide groups, aziridine groups, episulfide groups, groups such as $-CO_2N(COCH_2)_2$, $-CO_2N(COCH_2)_2$, $-CO_2H$, $-CHO$, $-CHOCH_2$, $-N=C=O$, $-SO_2CH=CH_2$, $-N(COCH)_2$, $-S-S-(C_5H_4N)$ and groups of the following structures, wherein X is halogen and R is hydrogen or $C_1$ to $C_4$ alkyl

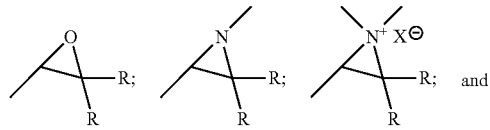

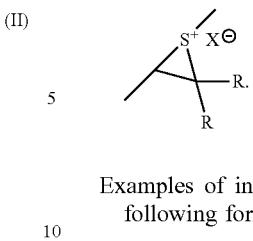

Examples of indolyl deoxyribose analogs can have the following formula (III):

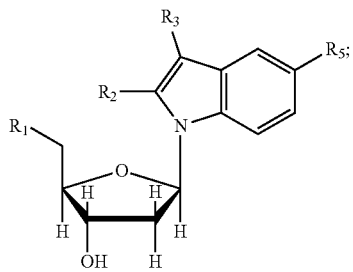

where $R_1$ is OH, monophosphate ($H_2O_3PO-$ or $(O_3PO-)^{2-}$), diphosphate ($H_3(O_3PO)_2-$ or $((O_3PO)_2-)^{3-}$), triphosphate ($H_4(O_3PO)_3-$, $((O_3PO)_3-)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate thereof;

where $R_5$ is a halo, (e.g., fluoro), amino, nitro, $C_3$-$C_{20}$ aryl (e.g., phenyl or napthyl), $C_1$-$C_{24}$ alkyl (e.g., ethyl, cyclohexyl), $C_2$-$C_{24}$ alkenyl (e.g., ethenyl, cyclohexenyl), substituted aryl, substituted alkenyl, or carboxyl; and where $R_2$ or $R_3$ is a click-reactive functional group selected from the group consisting of an amine, sulfate, thiol, hydroxyl, azide, alkyne, alkene, carboxyl groups, aldehyde groups, sulfone groups, vinylsulfone groups, isocyanate groups, acid anhydride groups, epoxide groups, aziridine groups, episulfide groups, groups such as $-CO_2N(COCH_2)_2$, $-CO_2N(COCH_2)_2$, $-CO_2H$, $-CHO$, $-CHOCH_2$, $-N=C=O$, $-SO_2CH=CH_2$, $-N(COCH)_2$, $-S-S-(C_5H_4N)$ and groups of the following structures, wherein X is halogen and R is hydrogen or $C_1$ to $C_4$ alkyl

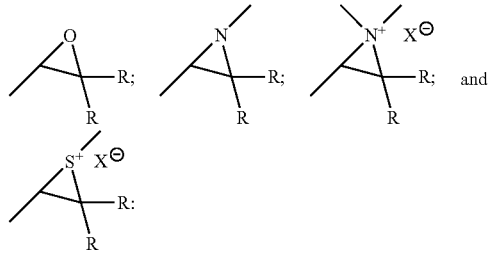

a pharmaceutically acceptable salt thereof, or a prodrug thereof.

In a further aspect, $R_5$ can be a substituent that has a π-electron surface area and density effective to facilitate base stacking interactions and enhance the efficiency for insertion of the agent opposite a non-templating DNA lesion. Examples of such substituents include nitro, ethenyl, cyclohexenyl, phenyl, biphenyl, and napthyl.

In still a further aspect, the theranostic agent can have the following formula:

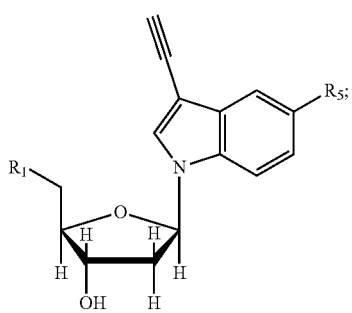

where $R_5$ is a halo, (e.g., fluoro), amino, nitro, $C_3$-$C_{20}$ aryl (e.g., phenyl or napthyl), $C_1$-$C_{24}$ alkyl (e.g., ethyl, cyclohexyl), $C_2$-$C_{24}$ alkenyl (e.g., ethenyl, cyclohexenyl), substituted aryl, substituted alkenyl, or carboxyl; or a pharmaceutically acceptable salt thereof.

In another subclass of theranostic agents, the adenine deoxyribose analog can comprise a purine deoxyribose analog that is substituted at the 2 and 6 position of the purine, such as shown in the following formula (IV):

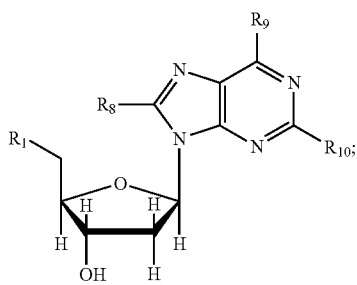

(IV)

where $R_1$ is OH, monophosphate ($H_2O_3PO-$ or $(O_3PO-)^{2-}$), diphosphate ($H_3(O_3PO)_2-$ or $((O_3PO)_2-)^{3-}$), triphosphate ($H_4(O_3PO)_3-$, $((O_3PO)_3-)^{4-}$), or $OR_a$, where $R_a$ comprises at least one of a straight chain, branched or cylclic alkyl, CO-alkyl, CO-aryl, CO-alkoxyalkyl, arylsulfonyl, aralkylsulfonyl, amino acid residude, fatty acid residue, or a mono, di, or triphosphate thereof;

where $R_9$ and $R_{10}$ each independently represent substituents selected from the group consisting of hydrogen, a halo, (e.g., fluoro), an amine, a substituted amine (HN—$CH_3$), nitro, $O_3$—$C_{20}$ aryl (e.g., phenyl or napthyl), $C_1$-$C_{24}$ alkyl (e.g., ethyl, cyclohexyl), $C_2$-$C_{24}$ alkenyl (e.g., ethylene, cyclohexene), substituted aryl, substituted alkenyl, carboxyl, or nitro, and where $R_9$ is amino $R_{10}$ is other than hydrogen; and where $R_8$ is a click-reactive functional group selected from the group consisting of an amine, sulfate, thiol, hydroxyl, azide, alkyne, alkene, carboxyl groups, aldehyde groups, sulfone groups, vinylsulfone groups, isocyanate groups, acid anhydride groups, epoxide groups, aziridine groups, episulfide groups, groups such as —$CO_2N(COCH_2)_2$, —$CO_2N(COCH_2)_2$, —$CO_2H$, —$CHO$, —$CHOCH_2$, —N=C=O, —$SO_2CH$=$CH_2$, —$N(COCH)_2$, —S—S—$(C_5H_4N)$ and groups of the following structures, wherein X is halogen and R is hydrogen or C, to $C_4$ alkyl

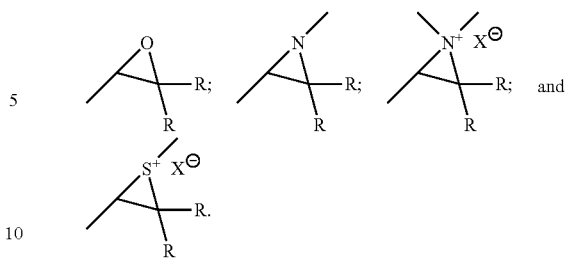

In a further subclass of therapeutic agents, the adenine deoxyribose analog can comprise a purine deoxyribose analog that is substituted at the 6 position of the purine analog, such as shown in the following formula (V):

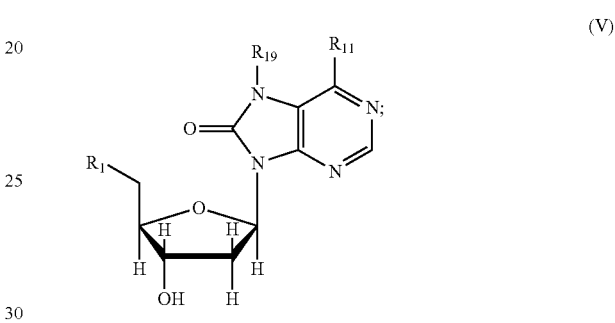

(V)

where $R_1$ is OH, monophosphate ($H_2O_3PO-$ or $(O_3PO-)^{2-}$), diphosphate ($H_3(O_3PO)_2-$ or $((O_3PO)_2-)^{3-}$), triphosphate ($H_4(O_3PO)_3-$, $((O_3PO)_3-)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue, fatty acid residue, or a mono, di, or triphosphate derivative;

where $R_{11}$ is hydrogen, a halo, (e.g., fluoro), an amine, a substituted amine (HN—$CH_3$), nitro, $C_3$-$C_{20}$ aryl (e.g., phenyl or napthyl), $C_1$-$C_{24}$ alkyl (e.g., ethyl, cyclohexyl), $C_2$-$C_{24}$ alkenyl (e.g., ethylene, cyclohexene), substituted aryl, substituted alkenyl, carboxyl, or nitro; and where $R_{19}$ is a click-reactive functional group selected from the group consisting of an amine, sulfate, thiol, hydroxyl, azide, alkyne, alkene, carboxyl groups, aldehyde groups, sulfone groups, vinylsulfone groups, isocyanate groups, acid anhydride groups, epoxide groups, aziridine groups, episulfide groups, groups such as —$CO_2N(COCH_2)_2$, —$CO_2N(COCH_2)_2$, —$CO_2H$, —CHO, —$CHOCH_2$, —N=C=O, —$SO_2CH$=$CH_2$, —$N(COCH)_2$, —S—S—$(C_5H_4N)$ and groups of the following structures, wherein X is halogen and R is hydrogen or $C_1$ to $C_4$ alkyl

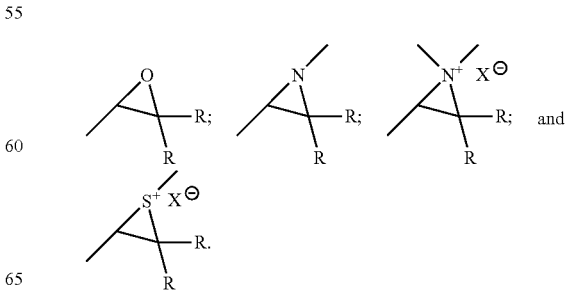

In yet another subclass of theranostic agents, the adenine deoxyribose analog can comprise a purine deoxyribose analog that is substituted at the 6 position of the purine, such as shown in the following formula (VI):

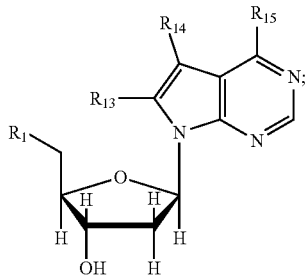

(VI)

where $R_1$ is OH, monophosphate ($H_2O_3PO$— or ($O_3PO$—)$^{2-}$), diphosphate ($H_3(O_3PO)_2$— or (($O_3PO)_2$—)$^{3-}$), triphosphate ($H_4(O_3PO)_3$—, (($O_3PO)_3$—)$^{4-}$), or $OR_a$, where $R_a$ comprises at least one of a straight chain, branched or cylclic alkyl, CO-alkyl, CO-aryl, CO-alkoxyalkyl, arylsulfonyl, aralkylsulfonyl, amino acid residude, fatty acid residue, or a mono, di, or triphosphate derivative;

where $R_{15}$ is selected from the group consisting of hydrogen, a halo, (e.g., fluoro), an amine, a substituted amine (HN—$CH_3$), nitro, $C_3$-$C_{20}$ aryl (e.g., phenyl or napthyl), $C_1$-$C_{24}$ alkyl (e.g., ethyl, cyclohexyl), $C_2$-$C_{24}$ alkenyl (e.g., ethylene, cyclohexene), substituted aryl, substituted alkenyl, carboxyl, or nitro; and where $R_{13}$ or $R_{14}$ is a click-reactive functional group selected from the group consisting of an amine, sulfate, thiol, hydroxyl, azide, alkyne, alkene, carboxyl groups, aldehyde groups, sulfone groups, vinylsulfone groups, isocyanate groups, acid anhydride groups, epoxide groups, aziridine groups, episulfide groups, groups such as —$CO_2N$ $(COCH_2)_2$, —$CO_2N(COCH_2)_2$, —$CO_2H$, —CHO, —$CHOCH_2$, —N=C=O, —$SO_2CH$=$CH_2$, —$N(COCH)_2$, —S—S—($C_5H_4N$) and groups of the following structures, wherein X is halogen and R is hydrogen or $C_1$ to $C_4$ alkyl

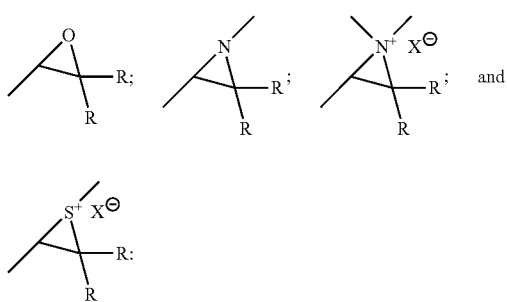

a pharmaceutically acceptable salt thereof, or a prodrug thereof.

In yet another subclass of theranostic agents, the adenine deoxyribose analog can comprise a purine deoxyribose analog that is substituted at the 6 position of the purine analog, such as shown in the following formula (VII):

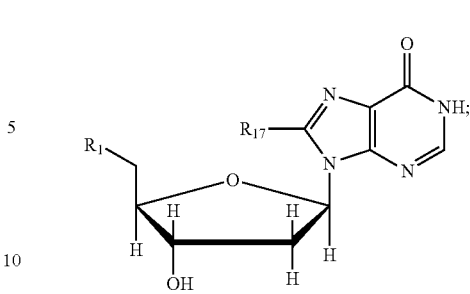

where $R_1$ is OH, monophosphate ($H_2O_3PO$— or ($O_3PO$—)$^{2-}$), diphosphate ($H_3(O_3PO)_2$— or (($O_3PO)_2$—)$^{3-}$), triphosphate ($H_4(O_3PO)_3$—, (($O_3PO)_3$—)$^{4-}$), or $OR_a$, where $R_a$ comprises at least one of a straight chain, branched or cylclic alkyl, CO-alkyl, CO-aryl, CO-alkoxyalkyl, arylsulfonyl, aralkylsulfonyl, amino acid residude, fatty acid residue, or a mono, di, or triphosphate derivative; and where $R_{17}$ is a click-reactive functional group selected from the group consisting of an amine, sulfate, thiol, hydroxyl, azide, alkyne, alkene, carboxyl groups, aldehyde groups, sulfone groups, vinylsulfone groups, isocyanate groups, acid anhydride groups, epoxide groups, aziridine groups, episulfide groups, groups such as —$CO_2N$ $(COCH_2)_2$, —$CO_2N(COCH_2)_2$, —$CO_2H$, —CHO, —$CHOCH_2$, —N=C=O, —$SO_2CH$=$CH_2$, —$N(COCH)_2$, —S—S—($C_5H_4N$) and groups of the following structures, wherein X is halogen and R is hydrogen or $C_1$ to $C_4$ alkyl

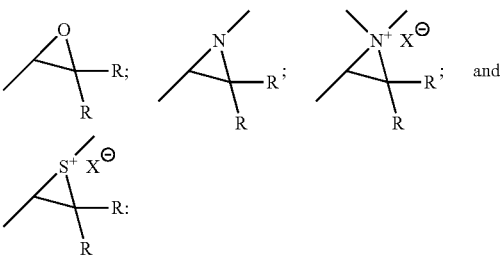

a pharmaceutically acceptable salt thereof, or a prodrug thereof.

The adenine deoxyriboside analogs of formula (I-VII) can be used as theranostic agents for the treatment or diagnosis of cancer in a subject. When used as theranostic agents, the adenine deoxyriboside analogs of formula (I-VII) can be conveniently formulated into pharmaceutical formulations composed of one or more of the compounds (i.e., adenine deoxyriboside analogs of formula (I-VII)) in association with a pharmaceutically acceptable carrier. (See Remington: The Science and Practice of Pharmacy, 19.sup.th Ed. (Easton, Pa.: Mack Publishing Co., 1995), which discloses typical carriers and conventional methods of preparing pharmaceutical formulations.)

The term "treatment" refers to reduction in severity and/or frequency of symptoms, elimination of symptoms and/or underlying cause, prevention of the occurrence of symptoms and/or their underlying cause, and improvement or remediation of damage. For example, treatment of a patient by administration of a theranostic agent described herein encompasses chemoprevention in a patient susceptible to developing cancer (e.g., at a higher risk, as a result of genetic predisposition, environmental factors, or the like) and/or in cancer survivors at risk of cancer recurrence, as well as treatment of a cancer patient by inhibiting or causing regression of a disorder or disease.

The adenine deoxyriboside analogs of formula (I-VII) can also be administered as a stabilized nucleotide prodrug to increase the activity, bioavailability, stability or otherwise alter the properties of the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, Antiviral Research, 27 (1995) 1-17. Any of these can be used in combination with the disclosed nucleosides to achieve a desired effect.

In one aspect, the adenine deoxyriboside analogs of formula (I-VII) can be provided as a 5'-hydroxyl lipophilic prodrug. Nonlimiting examples of U.S. patents that disclose suitable lipophilic substituents that can be covalently incorporated into the nucleoside, at the 5'-OH position of the nucleoside or lipophilic preparations, include U.S. Pat. No. 5,149,794; U.S. Pat. No. 5,194,654, U.S. Pat. No. 5,223,263; U.S. Pat. No. 5,256,641; U.S. Pat. No. 5,411,947; U.S. Pat. No. 5,463,092; U.S. Pat. No. 5,543,389; U.S. Pat. No. 5,543,390; U.S. Pat. No. 5,543,391; and U.S. Pat. No. 5,554,728, all of which are incorporated herein by reference.

The adenine deoxyribose analogs of formula (I-VII) may be administered orally, parenterally, rectally, vaginally, buccally, sublingually, nasally, by inhalation, topically, transdermally, or via an implanted reservoir in dosage forms containing conventional non-toxic pharmaceutically acceptable carriers and excipients. The term "parenteral" as used herein is intended to include subcutaneous, intravenous, and intramuscular injection. The amount of the adenine deoxyriboside analogs of formula (I-VII) administered can, of course, be a therapeutically effective amount and can be dependent on the particular active agent, the condition or disorder being treated, the severity of the condition or disorder, the subject's weight, the mode of administration and other pertinent factors known to the prescribing physician. Generally, however, dosage can be in the range of approximately 0.001 µg/mL/day to 100 µg/mL/day, more preferably in the range of about 0.1 µg/mL/day to 10 µg/ml/day.

Depending on the intended mode of administration, the pharmaceutical formulation may be a solid, semi-solid or liquid, such as, for example, a tablet, a capsule, caplets, a liquid, a suspension, an emulsion, a suppository, granules, pellets, beads, a powder, or the like, preferably in unit dosage form suitable for single administration of a precise dosage. Suitable pharmaceutical compositions and dosage forms may be prepared using conventional methods known to those in the field of pharmaceutical formulation and described in the pertinent texts and literature, e.g., in Remington: The Science and Practice of Pharmacy, cited above.

For those compounds that are orally active, oral dosage forms are generally preferred, and include tablets, capsules, caplets, solutions, suspensions and syrups, and may also comprise a plurality of granules, beads, powders or pellets that may or may not be encapsulated. Preferred oral dosage forms are tablets and capsules.

Tablets may be manufactured using standard tablet processing procedures and equipment. Direct compression and granulation techniques are preferred. In addition to the active agent, tablets can generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose, and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the active agent-containing composition may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, Remington: The Science and Practice of Pharmacy, cited supra, which describes materials and methods for preparing encapsulated pharmaceuticals.

Oral dosage forms, whether tablets, capsules, caplets, or particulates, may, if desired, be formulated so as to provide for gradual, sustained release of the active agent over an extended time period. Generally, as will be appreciated by those of ordinary skill in the art, sustained release dosage forms are formulated by dispersing the active agent within a matrix of a gradually hydrolyzable material such as an insoluble plastic (e.g., polyvinyl chloride or polyethylene), or a hydrophilic polymer, or by coating a solid, drug-containing dosage form with such a material. Hydrophilic polymers useful for providing a sustained release coating or matrix include, by way of example: cellulosic polymers such as hydroxypropyl cellulose, hydroxyethyl cellulose, hydroxypropyl methyl cellulose, methyl cellulose, ethyl cellulose, cellulose acetate, and carboxymethylcellulose sodium; acrylic acid polymers and copolymers, preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate; and vinyl polymers and copolymers such as polyvinyl pyrrolidone, polyvinyl acetate, and ethylene-vinyl acetate copolymer.

Preparations for parenteral administration include sterile nonaqueous solutions, suspensions, and emulsions. Examples of nonaqueous solvents or vehicles are propylene glycol, polyethylene glycol, vegetable oils, such as olive oil and corn oil, gelatin, and injectable organic esters such as ethyl oleate. Parenteral formulations may also contain adjuvants such as preserving, wetting, emulsifying, and dispersing agents. The formulations are rendered sterile by incorporation of a sterilizing agent, filtration through a bacteria-retaining filter, irradiation, or heat. They can also be manufactured using a sterile injectable medium.

The compound may also be administered through the skin or mucosal tissue using conventional transdermal drug delivery systems, wherein the active agent is contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. Transdermal drug delivery systems may in addition contain a skin permeation enhancer.

Although the present compounds can generally be administered orally, parenterally, or transdermally, other modes of administration are suitable as well. For example, administration may be rectal or vaginal, preferably using a suppository that contains, in addition to the active agent, excipients such cocoa butter or a suppository wax. Formulations for nasal or sublingual administration are also prepared with standard excipients well known in the art. The pharmaceutical compositions may also be formulated for inhalation, e.g., as a solution in saline, as a dry powder, or as an aerosol.

The adenine deoxyribose analogs of formula (I-VII) are of value in a number of methods. In some embodiments, methods of, and uses in, are provided for significantly inhibiting translesion DNA synthesis without substantially inhibiting normal DNA synthesis. The methods can comprise contacting a population of cells or tissues that include mutagenic DNA with a composition comprising a biologically effective amount of at least one adenine deoxyribose analog of formula (I-VII) under conditions effective to promote chain termination of the damaged DNA without substantially inhibiting normal DNA synthesis.

Additional embodiments include the use of the adenine deoxyribose analogs of the formula (I-VII) as an antiviral agent. The adenine deoxyribose analogs described herein can be administered to a population cells or tissue infected with a virus and inhibit or interfere with viral nucleic acid replication. The adenine deoxyribose analogs can be administered by contacting the infected cells with a composition comprising a biologically effective amount of at least one adenine deoxyribose analog of formula (I-VII) under conditions effective to inhibit viral replication.

Still further methods and uses are in analyzing the biological roles of the adenine deoxyribose analogs of formula (I-VII). In the method, a biological composition or tissue that comprises a population of cells that include mutagenic DNA are contacted with a composition comprising a biologically effective amount of at least of at least one of the theranostic agents. The effect of the theranostic agent on translesion DNA synthesis is then determined by administering the detectable moiety to the cells and measuring or quantifying the amount of adenine deoxyribose analogs of formula (I-VII) bound to DNA by detecting the detectable moiety using a suitable imaging modality.

The foregoing methods and uses can be performed in vitro and in vivo. In the latter case, where the tissues or cells are located within an animal, at least one of the adenine deoxyribose analogs of formula (I-VII) can be administered to the animal as a form of therapy. Where populations of cells with potentially mutagenic DNA are maintained ex vivo, analogs described herein have utility in drug discovery programs.

"Biologically effective amounts", in terms of each of the foregoing inhibitory methods are therefore amounts of the at least one of adenine deoxyribose analog of formula (I-VII) effective to inhibit translesion DNA synthesis, without substantially inhibiting normal DNA synthesis; and without being cytotoxic to the cells.

In a further aspect, the adenine deoxyribose analogs of formula (I-VII) can be used in combination and adjunctive therapies for treating mammalian diseases, such as in therapies in which potentially promutagenic therapeutic agents are administered to treat the disease.

The phrase "combination therapy" embraces the administration of the adenine deoxyribose analogs of formula (I-VII), and a therapeutic agent as part of a specific treatment regimen intended to provide a beneficial effect from the co-action of these therapeutic agents. Administration of these therapeutic agents in combination typically is carried out over a defined time period (usually minutes, hours, days or weeks depending upon the combination selected). "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients (such as, but not limited to, a second and different therapeutic agent) and non-drug therapies (such as, but not limited to, surgery or radiation treatment). Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

The phrase "adjunctive therapy" encompasses treatment of a subject with agents that reduce or avoid side effects associated with the combination therapy, including, but not limited to, those agents, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

The mammalian disease treated by the combination therapy can include proliferative diseases, such as neoplastic disorders (e.g., leukemia) and autoimmune dysfunctions as well as viral and microbial infections. Besides being useful for human treatment, the combination therapy is also useful for veterinary treatment of companion animals, exotic and farm animals, including rodents, horses, dogs, and cats.

In some embodiments, the therapeutic agent administered in combination therapy with the adenine deoxyribose analogs of formula (I-VII) can comprise cytoxic agents that can potentially compromise the integrity of nucleic acids associated with DNA replication and cellular proliferation (i.e., DNA damaging agents). The adenine deoxyribose analogs of formula (I-VII) as described herein are selective for damaged DNA and can potentiate the cytotoxic effects of the DNA damaging agents. Additionally, since the adenine deoxyribose analogs of formula (I-VII) behave as chain terminators, they can prevent propagation of genomic errors caused by the DNA damaging agents and would thus limit the development of resistance caused by replication of the mutated DNA. Moreover, the use of these therapeutic agents should not affect enzymatic phosphorylation, in contrast to other chain-terminators that have ribose modifications.

In another aspect, the therapeutic agents administered in combination therapy with the adenine deoxyribose analogs of formula (I-VII) can comprise at least one anti-proliferative agent selected from the group consisting of a chemotherapeutic agent, an antimetabolite, an antitumorgenic agent, an antimitotic agent, an antiviral agent, an antineoplastic agent, an immunotherapeutic agent, and a radiotherapeutic agent.

The phrase "anti-proliferative agent" can include agents that exert antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agent agents available in commercial use, in clinical evaluation and in pre-clinical development, which could be included by combination drug chemotherapy. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endothelial cells, selenium, stromelysin inhibitors, taxanes, vaccines, and *vinca* alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

A first family of anti-proliferative agents that may be used in combination therapy with the adenine deoxyribose analogs of formula (I-VII) consists of antimetabolite-type anti-proliferative agents. Antimetabolites are typically reversible or irreversible enzyme inhibitors, or compounds that otherwise interfere with the replication, translation or transcription of nucleic acids. Examples of antimetabolite antineoplastic agents that may be used include, but are not limited to acanthifolic acid, aminothiadiazole, anastrozole, bicalutamide, brequinar sodium, capecitabine, carmofur, Ciba-Geigy CGP-30694, cladribine, cyclopentyl cytosine, cytarabine phosphate stearate, cytarabine conjugates, cytarabine ocfosfate, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, finasteride, floxuridine, fludarabine phosphate, N-(2'-furanidyl)-5-fluorouracil, Daiichi Seiyaku FO-152, fluorouracil (5-FU), 5-FU-fibrinogen, isopropyl pyrrolizine, Lilly LY-188011, Lilly LY-264618, methobenzaprim, methotrexate, Wellcome MZPES, nafarelin, norspermidine, nolvadex, NCI NSC-127716, NCI NSC-264880, NCI NSC-39661, NCI NSC-612567, Warner-Lambert PALA, pentostatin, piritrexim, plicamycin, Asahi Chemical PL-AC, stearate; Takeda TAC-788, thioguanine, tiazofurin, Erbamont TIF, trimetrexate, tyrosine kinase inhibitors, tyrosine protein kinase inhibitors, Taiho UFT, toremifene, and uricytin, all of which are disclosed in U.S. Pat. No. 6,916,800, which is herein incorporated by reference in its entirety.

A second family of anti-proliferative agents that may be used in combination therapy with the analogs described herein consists of alkylating-type anti-proliferative agents. The alkylating agents are believed to act by alkylating and cross-linking guanine and possibly other bases in DNA, arresting cell division. Typical alkylating agents include nitrogen mustards, ethyleneimine compounds, alkyl sulfates, cisplatin, and various nitrosoureas. A disadvantage with these compounds is that they not only attack malignant cells, but also other cells which are naturally dividing, such as those of bone marrow, skin, gastro-intestinal mucosa, and fetal tissue. Examples of alkylating-type anti-proliferative agents that may be used include, but are not limited to, Shionogi 254-S, aldo-phosphamide analogues, altretamine, anaxirone, Boehringer Mannheim BBR-2207, bestrabucil, budotitane, Wakunaga CA-102, carboplatin, carmustine (BiCNU), Chinoin-139, Chinoin-153, chlorambucil, cisplatin, cyclophosphamide, American Cyanamid CL-286558, Sanofi CY-233, cyplatate, dacarbazine, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, etoposide phosphate, fotemustine, Unimed G-6-M, Chinoin GYKI-17230, hepsulfam, ifosfamide, iproplatin, lomustine, mafosfamide, mitolactol, mycophenolate, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, thiotepa, Yakult Honsha SN-22, spiromus-tine, Tanabe Seiyaku TA-077, tauromustine, temozolomide, teroxirone, tetraplatin and trimelamol.

A third family of anti-proliferative agents that may be used in combination therapy with the analogs described herein consists of antibiotic-type anti-proliferative agents. Examples of antibiotic-type anti-proliferative agents that may be used include, but are not limited to Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of anti-proliferative agents that may be used in combination therapy with the analogs described herein consists of synthetic nucleosides. Several synthetic nucleosides have been identified that exhibit anticancer activity. A well known nucleoside derivative with strong anticancer activity is 5-fluorouracil (5-FU). 5-Fluorouracil has been used clinically in the treatment of malignant tumors, including, for example, carcinomas, sarcomas, skin cancer, cancer of the digestive organs, and breast cancer. 5-Fluorouracil, however, causes serious adverse reactions such as nausea, alopecia, diarrhea, stomatitis, leukocytic thrombocytopenia, anorexia, pigmentation, and edema. Derivatives of 5-fluorouracil with anti-cancer activity have been described in U.S. Pat. No. 4,336,381, which is herein incorporated by reference in its entirety.

A fifth family of anti-proliferative agents that may be used in combination therapy with the analogs described herein consists of hormonal agents. Examples of hormonal-type anti-proliferative agents that may be used include, but are not limited to Abarelix; Abbott A-84861; Abiraterone acetate; Aminoglutethimide; anastrozole; Asta Medica AN-207; Antide; Chugai AG-041R; Avorelin; aseranox; Sensus B2036-PEG; Bicalutamide; buserelin; BTG CB-7598; BTG CB-7630; Casodex; cetrolix; clastroban; clodronate disodium; Cosudex; Rotta Research CR-1505; cytadren; crinone; deslorelin; droloxifene; dutasteride; Elimina; Laval University EM-800; Laval University EM-652; epitiostanol; episteride; Mediolanum EP-23904; EntreMed 2-ME; exemestane; fadrozole; finasteride; flutamide; formestane; Pharmacia & Upjohn FCE-24304; ganirelix; goserelin; Shire gonadorelin agonist; Glaxo Wellcome GW-5638; Hoechst Marion Roussel Hoe-766; NCI hCG; idoxifene; isocordoin; Zeneca ICI-182780; Zeneca ICI-118630; Tulane University J015X; Schering Ag J96; ketanserin; lanreotide; Milkhaus LDI-200; letrozol; leuprolide; leuprorelin; liarozole; lisuride hydrogen maleate; loxiglumide; mepitiostane; Leuprorelin; Ligand Pharmaceuticals LG-1127; LG-1447; LG-2293; LG-2527; LG-2716; Bone Care International LR-103; Lilly LY-326315; Lilly LY-353381-HCl; Lilly LY-326391; Lilly LY-353381; Lilly LY-357489; miproxifene phosphate; Orion Pharma MPV-2213ad; Tulane University MZ-4-71; nafarelin; nilutamide; Snow Brand NKS01; octreotide; Azko Nobel ORG-31710; Azko Nobel ORG-31806; orimeten; orimetene; orimetine; ormeloxifene; osaterone; Smithkline Beecham SKB-105657; Tokyo University OSW-1; Peptech PTL-03001; Pharmacia & Upjohn PNU-156765; quinagolide; ramorelix; Raloxifene; statin; sandostatin LAR; Shionogi S-10364; Novartis SMT-487; somavert; somatostatin; tamoxifen; tamoxifen methiodide; teverelix; toremifene; triptorelin; TT-232; vapreotide; vorozole; Yamanouchi YM-116; Yamanouchi YM-511; Yamanouchi YM-55208; Yamanouchi YM-53789; Schering AG ZK-1911703; Schering AG ZK-230211; and Zeneca ZD-182780.

A sixth family of anti-proliferative agents that may be used in combination therapy with the analogs described herein consists of a miscellaneous family of antineoplastic agents including, but not limited to alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, calcium carbonate, Calcet, Calci-Chew, Calci-Mix, Roxane calcium carbonate tablets, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Cell Pathways CP-461, Yakult Honsha CPT-11, crisnatol, curaderm, cytochalasin B, cytarabine, cytocytin, Merz D-609, DABIS maleate, dacarbazine, datelliptinium, DFMO, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel, Encore Pharmaceuticals E7869, elliprabin, elliptinium acetate, Tsumura EPMTC, ergotamine, etoposide, etretinate, Eulexin®, Cell Pathways Exisulind® (sulindac sulphone or CP-246), fenretinide, Merck Research Labs Finasteride, Florical, Fujisawa FR-57704, gallium nitrate, gemcitabine, genkwadaphnin, Gerimed, Chugai GLA-43, Glaxo GR-63178, grifolan NMF-5N, hexadecylphosphocholine, Green Cross HO-221, homoharringtonine, hydroxyurea, BTG ICRF-187, ilmofosine, irinotecan, isoglutamine, isotretinoin, Otsuka JI-36, Ramot K-477, ketoconazole, Otsuak K-76COONa, Kureha Chemical K-AM, MECT Corp KI-8110, American Cyanamid L-623, leucovorin, levamisole, leukoregulin, lonidamine, Lundbeck LU-23-112, Lilly LY-186641, Materna, NCI (US) MAP, marycin, Merrel Dow MDL-27048, Medco MEDR-340, megestrol, merbarone, merocyanine derivatives, methoxyamine, methylanilinoacridine, Molecular Genetics MGI-136, minactivin, mitonafide, mitoquidone, Monocal, mopidamol, motretinide, Zenyaku Kogyo MST-16, Mylanta, N-(retinoyl)amino acids, Nilandron; Nisshin Flour Milling N-021, N-acylated-dehydroalanines, nafazatrom, Taisho NCU-190, Nephro-Calci tablets, nocodazole derivative, Normosang, NCI NSC-145813, NCI NSC-361456, NCI NSC-604782, NCI NSC-95580, octreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, retinoids, Encore Pharmaceuticals R-flurbiprofen, Sandostatin; Sapporo Breweries RBS, restrictin-P, retelliptine, retinoic acid, Rhone-Poulenc RP-49532, Rhone-Poulenc RP-56976, Scherring-Plough SC-57050, Scherring-Plough SC-57068, seienium (selenite and selenomethionine), SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, Sugen SU-101, Sugen SU-5416, Sugen SU-6668, sulindac, sulindac sulfone; superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, Zileuton, ursodeoxycholic acid, and Zanosar.

The foregoing treatment methods and uses can generally involve the administration of a pharmaceutically effective composition of the adenine deoxyribose analogs of formula (I-VII) to the animal or patient systemically, such as by transdermal, intramuscular, intravenous injection and the like. However, any route of administration that allows the therapeutic agent to localize to the site or sites of the cells, which are being treated by the DNA damaging agent can be acceptable. Therefore, other suitable routes of delivery include oral, rectal, nasal, topical, and vaginal. U.S. Pat. No. 5,712,291, is incorporated herein by reference for purposes including further describing the various routes of administration that may be included in connection with the treatment of an angiogenic disease or disorder. For conditions associated with the eye, ophthalmic formulations and administration are contemplated.

"Administration", as used herein, means provision or delivery of the adenine deoxyribose analogs of formula (I) therapeutic agents in an amount(s) and for a period of time(s) effective to inhibit translesion DNA synthesis.

The "therapeutically effective amounts" are amounts adenine deoxyribose analogs of formula (I-VII) effective to inhibit translesion DNA synthesis and to potentiate the cytotoxic effects of the DNA damaging agent. Such effects are achieved without substantially inhibiting normal DNA synthesis in normal, healthy cells or tissues; and exerting negligible or manageable adverse side effects on normal, healthy cell or tissues of the animal or patient.

The adenine deoxyribose analogs of formula (I-VII) described herein can allow the combination therapeutic agents and therapies to be administered at a low dose, that is, at a dose lower than has been conventionally used in clinical situations. A benefit of lowering the dose of the combination therapeutic agents and therapies administered to a mammal includes a decrease in the incidence of adverse effects associated with higher dosages. For example, by the lowering the dosage of a chemotherapeutic agent such as methotrexate, a reduction in the frequency and the severity of nausea and vomiting will result when compared to that observed at higher dosages. Similar benefits are contemplated for the compounds, compositions, agents and therapies in combination with the inhibitors.

By lowering the incidence of adverse effects, an improvement in the quality of life of a patient undergoing treatment for cancer is contemplated. Further benefits of lowering the incidence of adverse effects include an improvement in patient compliance, a reduction in the number of hospitalizations needed for the treatment of adverse effects, and a reduction in the administration of analgesic agents needed to treat pain associated with the adverse effects. Alternatively, the methods and combination described herein can also maximize the therapeutic effect at higher doses.

When administered as a combination, the therapeutic agents can be formulated as separate compositions which are given at the same time or different times, or the therapeutic agents can be given as a single composition.

In some embodiments, the adenine deoxyribose analogs of formula (I-VII) can be used as theranostic or diagnostic agents to monitor the formation of DNA damage by antineoplastic agents and/or chemotherapeutic agents. By way of example, as illustrated in FIG. 1, adenine deoxyribose analogs of formula (I-VII), such as 3-Eth-5-NIdR, can be administered to cancer cells of the subject, such as leukemia cells, that are treated with DNA damaging agents that form abasic sites, such as alkylating agents (e.g., Methyl methanesulfonate (MMS), N-ethyl-N-nitrosourea (ENU), and temozolomide) and antifolates (e.g., methotrexate, pemetrexed, thymidylate synthase inhibitor, and 5-fluorouracil). The adenine deoxyribose analogs of formula (I-VII), such as 3-Eth-5-NIdR, can be selectively incorporated opposite non-templating DNA lesions and cause chain termination. A detectable moiety having a complementary click-reactive functional group to the click-reactive functional group of the adenine deoxyribose analogs of formula (I-VII) can then be administered to the subject. The detectable moiety once taken up by the cancer cells can react with the adenine deoxyribose analogs of formula (I-VII) and detected to measure or quantify the binding adenine deoxyribose analogs of formula (I-VII) to DNA of the cancer cells and measure, quantify, and/or monitor the generation of abasic sites by the DNA damaging agent and the effective of the DNA damaging agent. The amount of adenine deoxyribose analogs of formula (I-VII) bound to the DNA of cancer cells of the subject can be measured by visualizing a distribution of the adenine deoxyribose analogs of formula (I-VII) and detectable moieties in the subject (e.g., with an in vivo imaging modality as described herein), and then correlating the distribution of the with the efficacy of the anticancer agent in generating AP sites.

The number or amount of adenine deoxyribose analogs of formula (I-VII) bound to AP sites or DNA in cancer cells of the subject can be correlated with the amount of AP sites generated by the anticancer agent by comparing the number or amount of bound adenine deoxyribose analogs of formula (I-VII) to a predetermined value. The predetermined value can be based, for example, upon the number or amount of adenine deoxyribose analogs of formula (I-VII) bound to cancer cell lines after administration of the adenine deoxyribose analogs of formula (I-VII) but prior to administration of the anticancer agent. An increase or substantial increase in the number of bound adenine deoxyribose analogs of formula (I-VII) to AP sites of the cancer cells of the subject following administration of the anticancer agent is indicative of the anticancer agent being effective to generate AP sites in the cancer cells of the subject. Conversely, where the number of adenine deoxyribose analogs of formula (I-VII) bound to AP sites of the cancer cells is substantially the same or only moderately increased following administration of the anticancer agent, the anticancer is not effective or only moderately effective in generating AP sites in cancer cells of the subject.

In certain embodiments, the methods and adenine deoxyribose analogs of formula (I-VII) can be used in an intraoperative surgical procedure, such as a surgical tumor resection, to more readily define and/or image the cancer cell mass or volume during the surgery. In this aspect, the anticancer agent can be administered to the subject to generate AP sites in cancer cells and the adenine deoxyribose analogs of formula (I-VII) can be administered systemically or topically for in vivo imaging of the cancer cells during surgical procedures.

In other embodiments, the adenine deoxyribose analogs of formula (I-VII) can be used in a diagnostic method where a patient receives a fixed dose of anti-neoplastic or chemotherapeutic agent(s). After a fixed period of time, an aliquot of blood is removed. This sample is treated with the adenine deoxyribose analogs of formula (I-VII) and the detectable moiety and analyzed by imaging techniques to determine the amount of the adenine deoxyribose analog that has been incorporated into the DNA of all cells. The amount of nucleotide incorporation is directly correlated with the amount of DNA damaged caused by the initial treatment of chemotherapeutic agent. Based upon results of this assay, the clinician will be able to rationally modify the dose based upon empirical evidence of DNA damage. The speed of this assay will allow the clinician to rapidly modify the dose to improve the likelihood of a good patient response.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

In this Example, we show that 3-ethynyl-5-nitroindolyl-2'-deoxynucleoside triphosphate (3-Eth-5-NITP) functions as an efficient and potent chain-terminating nucleotide for the DNA polymerase, terminal deoxynucleotidyl transferase (TdT). In addition, we demonstrate that the corresponding nucleoside, 3-ethynyl-5-nitroindolyl-2'-deoxynucleoside (3-Eth-5-NIdR), functions as a novel theranostic anti-cancer agent against leukemia cells that overexpress TdT. The unique activities of this non-natural nucleoside against ALL highlights the selective inhibition of TdT activity. Potential clinical applications of this novel nucleoside analogue are discussed.

Methods

Preparation of 3-iodo-5-nitroindole (2)

A solution of $I_2$ (830 mg, 3.25 mmol) in anhydrous DMF (8 ml) was added into a solution of 5-nitroindole (1) (500 mg, 3.10 mmol) and KOH (440 mg, 7.75 mmol) in DMF (8 ml) at room temperature and stirred for 1.5 h under argon (See Scheme 1 below). The reaction mixture was immediately poured into water (200 ml) containing ammonia (0.5%) and sodium metabisulphite (0.1%) chilled at 0° C. The resulting precipitate was vacuum filtered and washed with cold water and vacuum dried in a desiccator overnight. The product was a bright yellow solid and the yield was 95%. $^1$H NMR (DMOS-$d_6$, 400 MHz, 298 K) δ: 7.70 (d, J=9.06 Hz, 1H, Ar), 7.95 (s, 1H, Ar), 8.15 (dd, J=8.98, 2.32 Hz, 1H, Ar), 8.28 (d, J=2.36 Hz, 1H, Ar), 12.31 (br s, 1H, N—H). $^{13}$C NMR (DMSO-$d_6$, 100 MHz, 298 K) δ: 59.6, 113.7, 117.7, 118.4, 130.0, 134.8, 140.3, 142.3. ESI-MS (+): calculated mass spectrum formula $C_8H_5IN_2O_2$ for M+Na: 310.9294; experimental mass spectrum: 310.9294.

Preparation of 3-iodo-5-nitroindolyl-2'-deoxyribose (3)

To an ice-chilled solution of (2) (700 mg, 2.4 mmol) dissolved in anhydrous acetonitrile (80 ml) was added NaH (173 mg, 7.2 mmol). The reaction mixture was then stirred at room temperature for an hour under argon prior to the addition of the Hoffer's chlorosugar, 1-α-chloro-3,5-di-(O-p-toluoyl)-2-deoxy-D-ribose (996 mg, 3.0 mmol), prepared as previously described, and was further stirred for 16 h. The solvent was then rota-evaporated under reduced pressure and the resulting crude product was immediately dissolved in anhydrous methanol (100 ml). To this solution was added anhydrous sodium methoxide until the pH is >12 and stirred at room temperature under argon atmosphere for 16 h. The solvent was evaporated under reduced pressure, and the crude product was purified by silica flash column chromatography using chloroform:methanol (90:10) as the eluent to yield 81% of bright yellow-orange solid. $^1$H NMR (DMSO-$d_6$, 400 MHz, 298 K) δ: 2.25-2.31 (m, 2H, 2'-H), 3.48-3.59 (m, 2H, 5'-H), 3.83-3.86 (m, 1-H, 4'-H), 4.34-4.38 (m, 1H, 3'-H), 4.99 (t, J=5.28 Hz, 1H, 5'-OH), 5.34 (d, J=4.13 Hz, 1H, 3'-OH), 6.44 ($t_{app}$, J=6.96 Hz, 1H, 1'-H), 7.89 (d, J=9.07 Hz, 1H, Ar), 8.09 (dd, J=9.13, 2.33 Hz, 1H, Ar), 8.12 (s, 1H, Ar), 8.16 (d, J=2.36 Hz, 1H, Ar). $^{13}$C NMR (DMSO-$d_6$, 100 MHz, 298 K) δ: 40.7, 61.6, 62.5, 71.4, 86.1, 88.5, 112.8, 118.0, 118.8, 130.9, 134.4, 139.9, 142.8. ESI-MS (+): calculated mass spectrum formula $C_{13}H_{13}IN_2NaO_5$ for M+Na: 426.9767; experimental mass spectrum: 426.9764.

Preparation of 3-[(trimethylsilyl)ethynyl]-5-nitroindolyl-2'-deoxyribose (4)

To a solution of (3) (250 mg, 0.60 mmol), $Pd(PPh_3)_2Cl_2$ (40 mg, 57 µmol) and CuI (27.6 mg, 147 µmol) dissolved in anhydrous THF (7.0 ml) was added triethylamine (0.24 ml, 1.7 mmol). To this reaction mixture was added dropwise trimethylsilylacetylene (0.42 ml, 2.9 mmol) over a period of 20 min and stirred at room temperature under argon for 3 h. The solvent was then evaporated under reduced pressure and the resulting oily residue was dissolved in EtOAc (50 ml) and washed with saturated KCl solution (50 ml). The organic layer was collected and further washed with 50 ml of 0.5M EDTA (pH=8.0), followed by another 50 ml of the saturated KCl solution. The organic layer was dried with $MgSO_4$, filtered through celite, and the solvent evaporated under reduced pressure to obtain a red-orange foam. The crude product was purified by silica flash column chromatography using ethyl acetate:methanol (90:10) as the eluent to yield 55% of red-orange foam. $^1$H NMR (DMSO-$d_6$, 400 MHz, 298 K) δ: 0.27 [s, 9H, Si(CH$_3$)$_3$], 2.27-2.33 (m, 2H, 2'-H), 3.49-3.60 (m, 2H, 5'-H), 3.84-3.87 (m, 1-H, 4'-H), 4.35-4.39 (m, 1H, 3'-H), 4.99 (t, J=5.27 Hz, 1H, 5'-OH), 5.35 (d, J=4.21 Hz, 1H, 3'-OH), 6.48 ($t_{app}$, J=6.94 Hz, 1H, 1'-H), 7.93 ($d_{app}$, J=9.07 Hz, 1H, Ar), 7.86 (dd, J=9.09, 2.47 Hz, 1H, Ar), 8.28 (s, 1H, Ar), 8.39 (dd, J=2.35, 0.36 Hz, 1H, Ar). ESI-MS (+): calculated mass spectrum formula $C_{18}H_{22}N_2O_5Si$ for M+H: 375.1376; experimental mass spectrum: 375.1384.

Preparation of 3-ethynyl-5-nitroindolyl-2'-deoxyribose (5)

To a degassed solution of (4) (120 mg) dissolved in anhydrous THF was added TBAF in THF (1.20 ml, 1 M) and stirred at room temperature under argon for 3 h. The solvent was evaporated under reduced pressure and the resulting crude product was purified by silica flash column chromatography using ethyl acetate:methanol (90:10) as the eluent to yield 80% of reddish foam. $^1$H NMR (DMSO-$d_6$, 400 MHz, 298 K) δ: 2.27-2.33 (m, 2H, 2'-H), 3.49-3.60 (m, 2H, 5'-H), 3.84-3.87 (m, 1-H, 4'-H), 4.35-4.39 (m, 1H, 3'-H), 4.37 (s, 1H, —C≡C—H), 5.00 (t, J=5.53 Hz, 1H, 5'-OH), 5.34 (d, J=4.34 Hz, 1H, 3'-OH), 6.47 ($t_{app}$, J=6.73 Hz, 1H, 1'-H), 7.92 (d, J=9.20 Hz, 1H, Ar), 8.11 (dd, J=9.20, 2.34 Hz, 1H, Ar), 8.27 (s, 1H, Ar), 8.39 (d, J=2.27 Hz, 1H, Ar). $^{13}$C NMR (DMSO-$d_6$, 100 MHz, 298 K) δ: 40.5, 62.1, 71.1, 76.3, 84.6, 85.9, 88.3, 99.5, 112.7, 116.1, 118.7, 128.9, 134.1, 138.4, 142.6. ESI-MS (+): calculated mass spectrum formula $C_{15}H_{14}N_2O_5$ for M+Na: 325.0800; experimental mass spectrum: 325.0799. UV (MeOH) $\lambda_{275}$ (nm): $\epsilon$=37 500 $cm^{-1}$ $M^{-1}$.

Preparation of 3-ethynyl-5-nitroindolyl-2'-deoxyribose-5'-triphosphate (6)

This compound was prepared as previously described using compound (5) as the starting material. The triphosphorylation process was initiated by forming the 50-monophosphorodichloridated intermediate by the dropwise addition of POCl3 in the reaction mixture containing (5) (0.07 mmol) and Proton Sponge (0.11 mmol) dissolved in 0.37 ml of trimethylphosphate pre-chilled at 0° C. The reaction was stirred for 2 h and monitored by TLC using the solvent system of 1-propanol:ammonium hydroxide:water (6:3:1). The reaction mixture was then spontaneously treated with 0.5M DMF solution of tributylammonium pyrophosphate (0.37 mmol) and tributylamine (0.37 mmol) and stirred for 15 min at room temperature. 1MTEAB was added to quench the reaction and stirred at room temperature for 2 h, then the crude product was evaporated by rota-evaporation under reduced pressure and purified by preparative reverse phase HPLC (mobile phase A: 0.1M TEAB; B: 35% ACN in 0.1M TEAB). The desirable nucleotide was lyophilized to dryness and characterized by mass spectrometry and $^{31}$P NMR. The isolated yield was ~30%. $^{31}$P-NMR ($D_2O$, 162 MHz) δ: −5.4 (γ-P), −10.2 (α-P), −21.3 (β-P). HiRes ESI-MS (−): calculated mass spectrum formula $C_{15}H_{15}N_2O_{14}P_3$ for [M–H]: 540.9820; spectral mass spectrum: 540.9830.

Polymerization Assays

All enzymatic assays were performed as previously described. Briefly, Vmax and Km values were determined using pseudo-first-order reaction conditions in which 6 units of TdT was preincubated with single-stranded DNA substrate (1.5 µM) in an assay buffer and mixed with variable concentrations of the nucleotide analogue (0.05-50 µM). Reactions were quenched with 200 Mm EDTA at variable times (5-600 s) and analyzed using denaturing gel electrophoresis. Time courses in product formation were fitted using eq 1:

$$Y = mt + b \quad (1)$$

where y is the amount of product, m is the rate of the reaction, t is time, and b is the Y-intercept. $K_m$ and $V_{max}$ values were determined by fits of the data points to the Michaelis-Menten equation:

$$\text{Rate} = \frac{V_{max}[dNTP]}{K_m + [dNTP]} \quad (2)$$

where $V_{max}$ is the maximal rate of nucleotide incorporation, $K_m$ is the Michaelis constant for dNTP, and [dNTP] is the concentration of nucleotide substrate. The $IC_{50}$ value for 3-Eth-5-NITP was obtained using a nonlinear regression curve fit of the data to eq 3:

$$Y = \frac{100\%}{1 + \frac{IC_{50}}{[\text{inhibitor}]}} \quad (3)$$

where Y is the fraction of TdT activity, IC is the concentration of 3-Eth-5-NITP to inhibit 50% TdT activity, and [inhibitor] is the concentration of 3-Eth-5-NITP tested. The Cheng-Prusoff equation (eq 4) was used to define a true Ki value for 3-Eth-5-NITP by normalizing the measured $IC_{50}$ value for the concentration of dNTPs and their corresponding Km values used in the experiments.

$$K_i \frac{IC_{50}}{1 + \frac{[dNTP]}{k_m[dNTP]}} \quad (4)$$

where $K_i$ is the true inhibition constant for 3-Eth-5-NITP, $IC_{50}$ is the concentration of 3-Eth-5-NITP that inhibits 50% TdT activity, [dNTP] is the concentration of nucleotide substrate and Km dNTP is the Michaelis constant for dNTP.

Cell Culture Procedures

All cells were cultured in a humidified atmosphere of 5% $CO_2$ at 37° C. MOLT4, Jurkat, J45.01, and RS4(11) cells were maintained in ATCC-formulated RPMI-1640 media supplemented with 10% fetal bovine serum (FBS), 5% L-glutamine, and 2.5% penicillin/streptomycin. Loucy and CEM-C7 cells were maintained in Cellgro formulated RPMI-1640 supplemented with 10% heat-inactivated FBS, 5% L-glutamine, and 2.5% penicillin/streptomycin antibiotic. Cells were routinely propagated and used for experiments in logarithmic phase.

Western Blot Analysis of TdT Present in ALL Cell Lines

Cell lysates from each ALL cell line were prepared in RIPA buffer (Thermo Fisher Scientific) containing a complete protease inhibitor cocktail tablet. The lysates (each with 50 µg of total protein content) were loaded on a Novex 4-20% Tris-Glycine gel, transferred into 0.2 µm nitrocellulose membrane and blocked with 1× Blocking buffer (Sigma-Aldrich) overnight at 4° C. The membrane was probed for TdT with primary antibody diluted in blocking solution (1:200) for 1 h at RT and then with a secondary donkey anti-goat IgG-HRP (1:5000 dilution) under identical conditions as the primary antibody. Immunoblots were developed by using enhanced chemiluminescence (Thermo Scientific), and the intensities of TdT and β-actin bands were quantified using the ImageJ program (http://imagej.nih.gov/ij/). TdT in each cell line was normalized by the corresponding β-actin content defined by Western blot analysis under identical conditions (TdT content=the intensity of TdT band divided by the intensity of β-actin band). Data represents an average of three independent determinations.

Cell Proliferation Assays

Cells were seeded at a population density of ~200,000 cells mL-1 and treated with variable concentrations of non-natural nucleoside (0.1-100 µg mL-1) for up to 72 h. The final DMSO concentration in all experiments was 0.1%. Cell viability was assessed via trypan blue staining and counting the number of viable (clear) versus non-viable (blue) cells under a microscopy using a hemocytometer. The IC$_{50}$ values for both nonnatural nucleosides were obtained using a nonlinear regression curve fit of the data to eq 3. LD$_{50}$ values for the non-natural nucleosides were calculated using identical approaches.

Apoptosis Measurements

Cells were treated with DMSO (vehicle), 5-NIdR (100 µg mL-1), and 3-Eth-5-NIdR (10 and 40 µg mL-1) as described above. Cells were harvested by centrifugation and washed in phosphate-buffered saline and resuspended in 100 µL of binding buffer containing AnnexinV-Alexa Fluor 488 conjugate. Cells were treated with propidium iodide (PI) and incubated at RT for 15 min followed by flow cytometry analysis. This enables live cells (unstained with either Alexa Fluor 488 or PI) to be discriminated from early apoptotic (stained with Alexa Fluor 488), late apoptotic cells (stained with Alexa Fluor 488 and PI), and necrotic cells (stained with PI).

In situ "click" reactions were performed using cells harvested after 2 days of treatment with DMSO, 3-Eth-5-NIdR (10, 40, or 100 µg mL$^{-1}$), 5-NIdR (100 µg mL$^{-1}$) or 5-ethynyl-2'-deoxyuridine (EdU) (10 µM). All cells were fixed with cold methanol. Under minimal lighting, cells were treated with 0.3 mL of saponin-based permeabilization and wash buffer for 45 min at 37° C. Click reactions were initiated by adding the click-iT reaction cocktail according to the instructions of the manufacturer (Invitrogen) followed by incubation at 37° C. for 90 min. Cells were then washed two times with saponin-based permeabilization and wash buffer. Cell pellets were dislodged using 0.5 mL solution of 10 µg mL$^{-1}$ PI and RNAase A in saponin-based permeabilization and wash buffer and then incubated for at least 15 min prior to flow cytometry analysis.

Results

Synthesis of a 'clickable' non-natural nucleoside and nucleoside triphosphate in Scheme 1 below was used to convert 5-NITP into a 'clickable' nucleotide designated 3-ethynyl-5-nitroindolyl-2'-deoxyribose-5'-triphosphate (3-Eth-5-NITP). This multi-step process begins with the installation of iodine at the 3-position of 5-nitroindole followed by N-glycosidic bond formation between 3-iodo-5-nitroindole and the Hoffer's chlorosugar using sodium hydride. Deprotection of the 3'- and 5'-hydroxyl moieties of the protected deoxyribose sugar was performed using Zemplén conditions. This reaction yields the β-anomeric isomer as the primary product as confirmed by nuclear-Overhauser effect (NOE) difference experiment (NOE's of H-2, H-7, H-2' and H-4' upon irradiation of H-1'). Furthermore, the presence of an apparent triplet (tapp) peak for the H-1' resonance with a coupling constant of ~7.0 Hz in the $^1$H NMR spectrum are also characteristics for the β-anomer of N-nucleosides. The iodine was then substituted with trimethylsilylacetylene using the Sonogashira reaction and eventually deprotected to obtain the free ethynyl functional group using 1M TBAF in THF. Conversion of 3-ethynyl-5-nitroindolyl-2'-deoxyribonucleoside to the corresponding triphosphate was accomplished by first reacting the nucleoside with POCl$_3$ to form the 5'-monophosphoro-dichloridated nucleoside intermediate which was then treated with pyrophosphate to form the nucleoside 5'-triphosphate. The crude product from this one-pot synthesis was purified via reverse-phase HPLC. The purified product was characterized by $^{31}$P-NMR and high resolution.

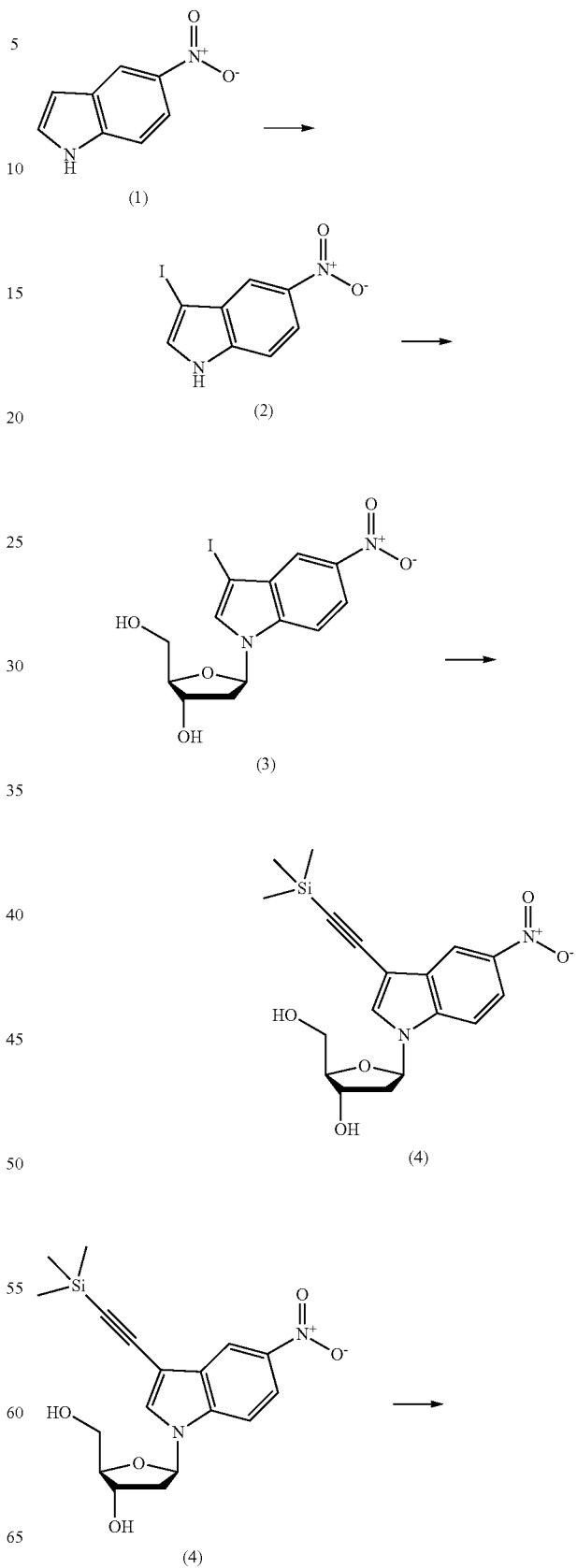

Scheme 1

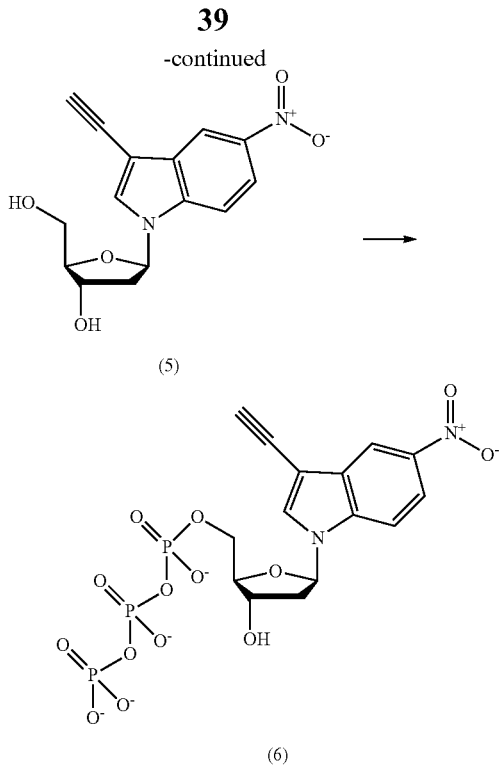

(5)

(6)

Utilization of Non-Natural Nucleotides by TdT

The biological function of TdT is to expand immunological diversity by randomly incorporating dNTPs into single-stranded DNA during V(D)J recombination. In vitro studies with purified TdT have demonstrated that while the polymerase utilizes all four natural dNTPs, there is a bias for incorporating dGTP and dCTP versus dATP and dTTP. TdT also utilizes nucleotide analogues including 2',3'-dideoxynucleotides, dinucleoside 5',5'-tetraphosphates, and intrinsically fluorescent nucleotide analogues. In this report, we tested if TdT also incorporates indolyl-2'-deoxyribose-5'-triphosphates that bear non-natural moieties such as ethynyl and nitro groups at the 3- and 5-position, respectively, of the indole base. Polymerization reactions were performed as outlined in FIG. 2A in which 100 µM of natural (dATP and dGTP) or non-natural (5-NITP or 3-Eth-5-NITP) nucleotides were added to a solution containing 6 units of TdT preincubated with 1.5 µM singlestranded DNA substrate (14-mer). Aliquots of the reaction were quenched with EDTA at variable time points, and the polymerization reactions were then subjected to denaturing polyacrylamide gel electrophoresis to separate extended primers from unreacted substrate. Representative data provided in FIG. 2B shows that both 5-NITP and 3-Eth-5-NITP are utilized by TdT as efficiently as the natural purines, dATP and dGTP as judged by the elongation of 14-mer DNA substrate to longer products.

The utilization of 5-NITP and 3-Eth-5-NITP by TdT was further quantified by measuring the kinetic parameters, $K_m$, $V_{max}$, and $V_{max}/K_m$. Time courses in product formation were generated using pseudo-first order reaction conditions in which 6 units of TdT were incubated with 1.5 µM DNA substrate and mixed with variable concentrations of non-natural nucleotide (0.05-50 µM). Each time course was fit to an equation for a straight line to define the rate of nucleotide incorporation (data not shown). The resulting plot of rate versus 3-Eth-5-NITP concentration is hyperbolic (FIG. 2C), and a fit of the data to the Michaelis-Menten equation yields a $V_{max}$ of 3.2±0.1 nM s$^{-1}$, a $K_m$ of 0.19±0.04 µM, and a $V_{max}/K_m$ of 0.0168±0.0004 s$^{-1}$. Identical experiments performed with 5-NITP yield a $V_{max}$ of 11.5±0.4 nM s$^{-1}$, a $K_m$ of 4.6±0.6 µM, and a $V_{max}/K_m$ of 0.0025±0.0003 s$^{-1}$ (FIG. 2D).

Table 1 summarizes the kinetic parameters for the utilization of natural and non-natural nucleotides by TdT. The catalytic efficiencies for 5-NITP and dATP are essentially identical, thus confirming reports that hydrogen-bonding interactions are not required by TdT for efficient DNA synthesis. More importantly, the catalytic efficiency for 3-Eth-5-NITP is 7-fold higher than that for 5-NITP. This enhancement is caused by a 24-fold decrease in the $K_m$ for 3-Eth-5-NITP that offsets a 3.5-fold decrease in $V_{max}$. This result is noteworthy as similar effects on $K_m$ were observed for incorporating 3-Eth-5-NITP opposite an abasic site. These results highlight the universal requirement of nucleobase hydrophobicity and n-electron interactions during template-independent DNA synthesis. However, one important distinction is that TdT extends beyond 5-NITP with an overall efficiency that rivals that of the natural purines, dATP and dGTP (FIG. 2B). In contrast, 3-Eth-5-NITP is poorly extended (FIG. 2B), indicating that it behaves as a universal chain terminator of DNA synthesis. Indeed, extension beyond 3-Eth-5-NITP is not observed, even after longer reaction times of up to 20 min.

TABLE 1

Summary of Kinetic Parameters for the Incorporation of Natural and Non-natural Nucloetides by Terminal Deoxynucleotidyl and Transferase

| dXTP | $K_m$ (µM) | $V_{max}$ (nM s$^{-1}$) | $V_{max}/K_m$ (s$^{-1}$) |
| --- | --- | --- | --- |
| dATP | 1.5 ± 0.4 | 3.3 ± 0.3 | 0.0022 ± 0.0005 |
| dGTP | 8.0 ± 0.9 | 29.2 ± 1.1 | 0.0037 ± 0.0005 |
| 5-NITP | 4.6 ± 0.06 | 11.5 ± 0.4 | 0.0025 ± 0.0003 |
| 3-Eth-5-NITP | 0.19 ± 0.04 | 3.2 ± 0.1 | 0.0168 ± 0.0004 |

The ability of 3-Eth-5-NITP to terminate DNA synthesis catalyzed by TdT was further evaluated through a series of competition experiments. TdT was preincubated with singlestranded DNA substrate and then mixed with a solution containing 10 µM dNTPs in the absence and presence of variable concentrations of 3-Eth-5-NITP (0.5-50 µM). Reactions were terminated after 3 min by adding 200 mM EDTA, and the replication products were separated via denaturing gel electrophoresis. Representative data provided in FIG. 2E shows that in the absence of 3-Eth-5-NITP, TdT randomly incorporates dNTPs to generate replication products with lengths ranging from $DNA_{n+1}$ to $DNA_{n+5}$. As the concentration of 3-Eth-5-NITP is increased, there is a concomitant decrease in the amount of replication products greater than $DNA_{n+1}$. Note that under these conditions, products corresponding to $DNA_{n+1}$ accumulate since 3-Eth-5-NITP is a non-extendable nucleotide substrate for TdT (vide supra). As such, the percent TdT activity as a function of 3-Eth-5-NITP concentration was plotted (FIG. 2F), and the resulting sigmoidal curve was fit to eq 3 to yield an $IC_{50}$ value of 3.9±1.0 µM for 3-Eth-5-NITP. A true $K_i$ value for 3-Eth-5-NITP of 0.51±0.13 µM was obtained using the Cheng-Prusoff equation (eq 4) to normalize this $IC_{50}$ value for the concentration of dNTPs and their corresponding $K_m$ values. The calculated $K_i$ value of 0.51 µM for 3-Eth-5-NITP is in good agreement with the $K_m$ value of 0.19 µM measured through initial velocity studies (Table 1). Collectively, these data indicate that 3-Eth-5-NITP is a bona fide chain-terminating substrate for TdT, even in the presence of physiological concentrations of dNTPs.

Defining the Potency of Non-Natural Nucleosides Against ALL Cell Lines

The facile utilization and chain termination capabilities of 3-Eth-5-NITP against TdT suggest that it may have therapeutic potential against ALL. This hypothesis was tested by measuring the cytostatic and/or cytotoxic effects of the corresponding nucleoside, 3-Eth-5-NIdR, and 5-nitroindolyl-2'-deoxynucleoside (5-NIdR) against various ALL cell lines including MOLT4, CEM-C7, Jurkat, RS4(11), JS45.01, and Loucy. Western blot analyses was first performed to determine TdT levels in each ALL cell line. As illustrated in FIG. 3A, each cell line contains variable levels of TdT, ranging from none (Loucy) to low (Jurkat, RS4(11)) to high (MOLT4, JS45.01, and CEM-C7). We next tested the efficacy of 5-NIdR and 3-Eth-5-NIdR by treating exponentially growing cells with variable concentrations (0.1-100 μg mL$^{-1}$) of each non-natural nucleoside for time periods of up to 3 days. Initial experiments used the MOLT4 cell line since this ALL cell line displays resistance to various chemotherapeutic agents due to higher levels of TdT. FIG. 3B provides representative time courses for the number of viable (left panel) and non-viable (right panel) MOLT4 cells in the absence and presence of 100 μg mL$^{-1}$ 5-NIdR or 3-Eth-5-NIdR (10 and 40 μg mL$^{-1}$). Treatment with 100 μg mL$^{-1}$ of 5-NIdR produces robust cytostatic and cytotoxic effects as early as 2 days post-treatment. In this case, the number of viable cells is reduced ~5-fold while there is a 2.5-fold increase in the number of non-viable cells. Analyses of the time courses in cell growth as a function of nucleoside concentration yield an IC$_{50}$ of 36.4±5.8 μg mL$^{-1}$ and an LD$_{50}$ value of ~100 μg mL$^{-1}$ for 5-NIdR. More striking effects are observed with 3-Eth-5-NIdR as cytostatic and cytotoxic effects are observed at a low concentration of 10 μg mL$^{-1}$ (FIG. 3B). These effects are also dose-dependent as treatment with μg mL$^{-1}$ shows a significant reduction in the number of viable cells coupled with a substantial increase in the number of non-viable cells (FIG. 3B). Quantitative analyses of the data yield an IC$_{50}$ of 14.1±2.4 μg mL$^{-1}$ and an LD$_{50}$ value 27.7±1.7 μg mL$^{-1}$ value for 3-Eth-5-NIdR.

To interrogate if the cytostatic and cytotoxic effects of 5-NIdR and 3-Eth-5-NIdR are dependent upon the cellular level of TdT, we next measured their effects against the TdT negative Loucy cell line (vide supra). Data provided in FIG. 3C show that both non-natural nucleosides are significantly less potent against this TdT-negative leukemia cell line compared to the TdT-positive cell line, MOLT4. In particular, treatment with 100 μg mL$^{-1}$ of 5-NIdR produces only a weak cytostatic effect as the number of viable cells is reduced by <25%. In addition, treatment with 5-NIdR does not cause a substantial increase in the number of non-viable cells. 3-Eth-5-NIdR is also ineffective as significant cytostatic or cytotoxic effects are not observed at a concentration of 40 μg mL$^{-1}$.

Identical cell-based experiments were performed with the other ALL cell lines, and the corresponding IC$_{50}$ and LD$_{50}$ values for 5-NIdR and 3-Eth-5-NIdR against each cell line are summarized in Table 2. Inspection of these data indicates that 3-Eth-5-NIdR is more potent than the parental nucleoside, 5-NIdR. The increased potency of 3-Eth-5-NIdR likely reflects the higher catalytic efficiency for the corresponding nucleoside triphosphate to act as a chain-terminating substrate for TdT. Consistent with this mechanism, the data also show that 3-Eth-5-NIdR displays higher potency against ALL cells that overexpress TdT compared to cells with lower TdT levels. This is best illustrated in FIG. 3D, which shows a linear relationship between the IC$_{50}$ values of 3-Eth-5-NIdR in various ALL cell lines as a function of cellular TdT content in each respective cell line. In general, there is an excellent correlation (R$^2$=0.695, p<0.0001) between the anti-cancer effects of the non-natural nucleoside with TdT level. Similar analyses were performed by plotting the LD50 values of 3-Eth-5-NIdR as a function of TdT content (FIG. 3E). These data also highlight a correlative effect between the cell killing effects of the nonnatural nucleoside with the cellular content of the TdT, the proposed molecular target for the corresponding chain-terminating nucleotide substrate.

TABLE 2

Summary of IC50 and LD50 of the Non-natural Nucleosides against Acute Lymphoblastic Leukemia Cell Lines

| Nucleoside | Cell line | IC$_{50}$ (μg mL$^{-1}$) | LD$_{50}$ (μg mL$^{-1}$) |
| --- | --- | --- | --- |
| 5-NIdR | MOLT4 | 34 ± 6 | ~100 |
| 3-Eth-5-NIdr | MOLT4 | 14 ± 2 | 28 ± 4 |
| 5-NIdR | Loucy | >>100 | >>100 |
| 3-Eth-5-NIdr | Loucy | 62 ± 5 | 63 ± 3 |
| 5-NIdR | CEM-C7 | ~100 | >>100 |
| 3-Eth-5-NIdr | CEM-C7 | 23 ± 2 | ~100 |
| 5-NIdR | Jurkat | ~100 | >>100 |
| 3-Eth-5-NIdr | Jurkat | 49 ± 1 | ~100 |
| 5-NIdR | RS4(11) | >100 | >>100 |
| 3-Eth-5-NIdr | RS4(11) | 23 ± 2 | 57 ± 2 |
| 5-NIdR | J45.01 | ~100 | >>100 |
| 3-Eth-5-NIdr | J45.01 | 34 ± 6 | 71 ± 6 |

Defining the Mechanism of Cell Death Induced by Non-Natural Nucleosides

The mechanism by which these non-natural nucleosides induce cell death was interrogated using dual parameter FACS analyses measuring propidium iodide uptake and Alexa Fluor488 annexin V conjugate staining. This allows live cells (unstained with either fluorophore) to be distinguished from cells that are early apoptotic (annexin V staining only), late apoptotic (propidium iodide and annexin V staining), and necrotic (propidium iodide staining only). Representative data provided in FIG. 3F shows that MOLT4 cells treated with 5-NIdR have higher levels of early and late stage apoptosis compared to cells treated with DMSO. In this case, treatment with 100 μg mL$^{-1}$ 5-NIdR causes a 5-fold increase in early and late stage apoptosis, respectively. Data summarized in Table 3 shows that the "clickable" nucleoside, 3-Eth-5-NIdR, is significantly more potent as treatment with 10 μg mL$^{-1}$ causes equivalent levels of apoptosis, while treatment with 40 μg mL$^{-1}$ results in 13- and 7-fold increases in early stage and late stage apoptosis, respectively. Furthermore, cells treated with either 5-NIdR or 3-Eth-5-NIdR show no significant PI uptake, thus indicating that neither non-natural nucleoside causes necrotic cell death. The induction of apoptosis was also independently confirmed by using agarose gel electrophoresis to observe DNA cleavage sites between nucleosomes that occur in chromatin at ~200-base pair intervals.

TABLE 3

Summary of Viable, Apoptotic, and Necrotic MOLT4 Cells after treatment with Non-natural nucleosides

| Condition | Viable cells (%) | Early apoptoic cells (%) | Late apoptoic cells (%) | Necrotic cells (%) |
|---|---|---|---|---|
| DMSO | 89.9 ± 0.9 | 5.4 ± 0.1 | 3.5 ± 1.1 | 1.2 ± 0.3 |
| 100 µg mL$^{-1}$ 5-NIdR | 53.1 ± 6.7 | 26.5 ± 3.7 | 18.9 ± 3.4 | 1.5 ± 0.5 |
| 10 µg mL$^{-1}$ 3-Eth-5-NIdR | 83.4 ± 2.7 | 10.5 ± 1.5 | 5.4 ± 1.0 | 0.7 ± 0.2 |
| 40 µg mL$^{-1}$ 3-Eth-5-NIdR | 6.3 ± 3.7 | 68.8 ± 0.9 | 23.7 ± 4.9 | 1.2 ± 0.2 |

Diagnostic Activities of Non-Natural Nucleosides

Cellbased experiments were performed to demonstrate that the "clickable" nucleoside, 3-Eth-5-NIdR, functions as a spectroscopic probe to measure the cellular activity of TdT. MOLT4 cells were treated with DMSO, EdU (a "clickable" thymidine analogue), 5-NIdR, and 3-Eth-5-NIdR for 2 days and then washed with PBS to remove any nucleoside and/or nucleotide not incorporated into DNA. After fixation and permeabilization, the cells were treated with AlexaFluor488-azide and Cu(I) catalyst to commence "clicking" of any incorporated nonnatural nucleotide. Dual parameter flow cytometry applying PI staining coupled with detection of the AlexaFluor488 fluorophore was used to detect the "clicked" non-natural nucleotide in cellular DNA. Cells treated with DMSO have a low level (<0.5%) of AlexaFluor488 stained DNA, while cells treated with 10 µM EdU show significantly higher levels (36.1%). This high amount of "clicked" DNA reflects transport of EdU into the cell, conversion to the corresponding nucleoside triphosphate, and incorporation into the DNA of replicating cells. MOLT4 cells treated with 10 µg mL$^{-1}$ 3-Eth-5-NIdR also show appreciable levels of AlexaFluor488 stained DNA (2.8%) after 2 days of treatment. Furthermore, the amount of "clicked" DNA is dosedependent as treatment with 40 µg mL$^{-1}$ Eth-5-NIdR yields a 2.5-fold increase in AlexaFluor488 staining (6.5%). Identical experiments were performed using the Loucy cell line that lacks TdT and thus is less sensitive to the cytotoxic effects of the non-natural nucleoside (vide inf ra). Data provided show that Loucy cells treated with DMSO have low levels of AlexaFluor488 staining (0.13%), while cells treated with 10 µM EdU have significantly higher levels (59.2%). Treatment with 40 µg mL$^{-1}$ of 3-Eth-5-NIdR produces low levels of "clicked" DNA (0.02%). These levels are significantly lower than those measured in MOLT4 cells under identical conditions and again correlate well with the lack of measurable TdT activity in the Loucy cell line. Collectively, these data are consistent with the mechanism outlined in FIG. 4C in which the non-natural nucleoside enters the cell via the activity nucleoside transporters, undergoes catabolism to the corresponding nucleoside triphosphate, and is then utilized by TdT. Once incorporated into DNA, the non-natural nucleotide inhibits cellular DNA replication and induces apoptosis. Finally, it should be emphasized that low levels (<0.5%) of AlexaFluor488 staining are detected in cells treated with 100 µg mL$^{-1}$ 5-NIdR. While this result could reflect a lack of stable incorporation of the non-natural nucleotide into DNA, it is more likely that the lack of the ethynyl moiety precludes covalent attachment of the azide-containing dye.

From the above description of the application, those skilled in the art will perceive improvements, changes and modifications. For example, it will be appreciated that the present application may find application in various other capacities, such as flow cytometry, affinity column chromatography, and the like. Such improvements, changes, and modifications are within the skill of those in the art and are intended to be covered by the appended claims. All patents, patent applications, and publication cited herein are incorporated by reference in their entirety.

We claim:

1. A method of adding a non-standard 2'-deoxynucleotide 5'-triphosphate to DNA in cells of a subject in need thereof, comprising:
   obtaining a biological sample containing cancer cells over expressing terminal deoxynucleotidyl transferase (TdT) from the subject; and
   treating the sample with an agent having the formula:

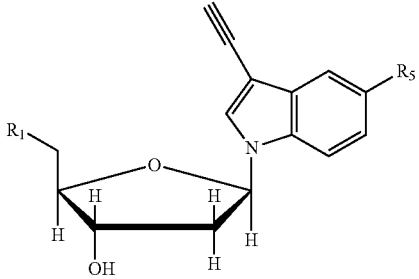

where $R_1$ is OH, monophosphate ($H_2O_3PO-$ or $(O_3PO-)^{2-}$), diphosphate ($H_3(O_3PO)_2-$ or $((O_3PO)_2-)^{3-}$), triphosphate ($H_4(O_3PO)_3-$, $((O_3PO)_3-)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue or fatty acid residue; and where $R_5$ is a nitro; or a pharmaceutically acceptable salt thereof;
   administering to the cancer cells treated with the agent a detectable moiety, which includes an azide group complementary to the alkyne group of the agent and a Cu catalyst; and detecting the detectable moiety bound to the agent.

2. The method of claim 1, the detectable moiety comprising a fluorophore with an azide group.

3. The method of claim 1, wherein the detectable moiety is selected from the group consisting of chromophore, luminophore, fluorophore, quantum dot or nanoparticle light scattering label, electromagnetic spin label, calorimetric agent, magnetic substance, electron-rich material metal, electrochemiluminescent label, light scattering or plasmon resonant materials, and affinity tags including enzyme and substrate reporter groups.

4. A kit comprising:
   (i) a compound having the formula:

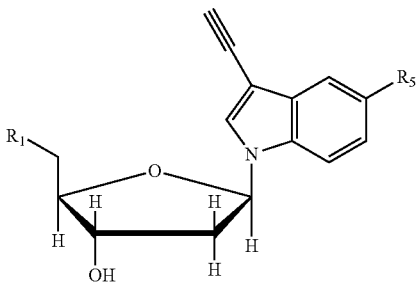

where $R_1$ is OH, monophosphate ($H_2O_3PO-$ or $(O_3PO-)^{2-}$), diphosphate ($H_3(O_3PO)_2-$ or $((O_3PO)_2-)^{3-}$), triphosphate ($H_4(O_3PO)_3-$, $((O_3PO)_3-)^{4-}$), or $OR_a$, where $R_a$ comprises at least one of a straight chain, branched or cyclic alkyl, CO-alkyl, CO-aryl, CO-alkoxyalkyl, arylsulfonyl, aralkylsulfonyl, amino acid residue or fatty acid residue; and where $R_5$ is a nitro; or a pharmaceutically acceptable salt thereof; and (ii) a detectable moiety with a click-reactive functional group that is complementary to the alkyne group of the compound.

5. The kit of claim 4, wherein the detectable moiety includes a fluorophore with an azide group.

6. The kit of claim 4, wherein the detectable moiety is selected from the group consisting of chromophore, luminophore, fluorophore, quantum dot or nanoparticle light scattering label, electromagnetic spin label, calorimetric agent, magnetic substance, electron-rich material metal, electrochemiluminescent label, light scattering or Plasmon resonant materials, and affinity tags including enzyme and substrate reporter groups.

* * * * *

SEQUENCE LISTING

<160> NUMBER OF SEQ ID NOS: 6

<210> SEQ ID NO 1
<211> LENGTH: 14
<212> TYPE: DNA
<213> ORGANISM: Artificial Sequence
<220> FEATURE:
<223> OTHER INFORMATION: Synthetic Construct

<400> SEQUENCE: 1
tcgcagccgt ccaa                                                        14

<210> SEQ ID NO 2
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (15)..(15)
<223> OTHER INFORMATION: 1 Non-Natural Nucleoside

<400> SEQUENCE: 2
tcgcagccgt ccaan                                                    15

<210> SEQ ID NO 3
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (15)..(16)
<223> OTHER INFORMATION: 2 Non-Natural Nucleosides

<400> SEQUENCE: 3
tcgcagccgt ccaann                                                   16

<210> SEQ ID NO 4
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (15)..(17)
<223> OTHER INFORMATION: 3 Non-Natural Nucleosides

<400> SEQUENCE: 4
tcgcagccgt ccaannn                                                  17

<210> SEQ ID NO 5
<211> LENGTH: 18
<212> TYPE: DNA
<213> ORGANISM: Artificial Sequence
<220> FEATURE:
<223> OTHER INFORMATION: Synthetic Constructs
<220> FEATURE:
<221> NAME/KEY: misc_feature
<222> LOCATION: (15)..(18)
<223> OTHER INFORMATION: 4 Non-Natural Nucleosides

<400> SEQUENCE: 5
tcgcagccgt ccaannnn                                                 18

<210> SEQ ID NO 6
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (15)..(19)
<223> OTHER INFORMATION: 5 Non-Natural Nucleosides

<400> SEQUENCE: 6
tcgcagccgt ccaannnnn                                                19